(12) United States Patent
Fortson

(10) Patent No.: US 10,980,981 B2
(45) Date of Patent: Apr. 20, 2021

(54) PROCEDURAL SHEATH

(71) Applicant: Abbott Cardiovascular Systems, Inc., Santa Clara, CA (US)

(72) Inventor: Aaron M. Fortson, Fremont, CA (US)

(73) Assignee: ABBOTT CARDIOVASCULAR SYSTEMS, INC, Santa Clara, CA (US)

(*) Notice: Subject to any disclaimer, the term of this patent is extended or adjusted under 35 U.S.C. 154(b) by 233 days.

(21) Appl. No.: 15/968,450

(22) Filed: May 1, 2018

(65) Prior Publication Data
US 2019/0336731 A1 Nov. 7, 2019

(51) Int. Cl.
*A61M 25/06* (2006.01)
*A61M 25/00* (2006.01)

(52) U.S. Cl.
CPC .... *A61M 25/0662* (2013.01); *A61M 25/0097* (2013.01); *A61M 2210/005* (2013.01); *A61M 2210/12* (2013.01)

(58) Field of Classification Search
CPC .......... A61M 25/0662; A61M 25/0097; A61M 2210/12; A61M 2210/005; A61M 2025/0059; A61M 2025/006; A61M 25/04; A61M 25/007
See application file for complete search history.

(56) References Cited

U.S. PATENT DOCUMENTS

| | | | | |
|---|---|---|---|---|
| 4,014,317 A | * | 3/1977 | Bruno | A61M 1/1037 600/18 |
| 4,648,871 A | | 3/1987 | Jacob | |
| 4,717,379 A | | 1/1988 | Ekholmer | |
| 4,846,810 A | * | 7/1989 | Gerber | B65D 1/32 604/247 |
| 4,973,321 A | | 11/1990 | Michelson | |
| 5,025,778 A | | 6/1991 | Silverstein et al. | |
| 5,092,855 A | * | 3/1992 | Pardes | B65D 47/205 604/247 |
| 5,135,517 A | * | 8/1992 | McCoy | A61B 17/320783 604/531 |
| 5,180,364 A | | 1/1993 | Ginsburg | |
| 5,353,783 A | | 10/1994 | Nakao et al. | |
| 5,573,520 A | | 11/1996 | Schwartz et al. | |
| 5,840,067 A | * | 11/1998 | Berguer | A61M 25/04 604/104 |
| 5,851,171 A | | 12/1998 | Gasson | |
| 6,179,813 B1 | | 1/2001 | Ballow et al. | |
| 6,387,056 B1 | * | 5/2002 | Kieturakis | A61B 10/0266 600/565 |
| 6,589,214 B2 | * | 7/2003 | McGuckin, Jr. | A61M 25/0662 604/165.03 |

(Continued)

*Primary Examiner* — Julian W Woo
(74) *Attorney, Agent, or Firm* — Workman Nydegger; Randy Shen

(57) ABSTRACT

A procedural sheath and methods of use that assists in maintaining a fluid path while the procedural sheath is positioned within a vascular conduit of a patient. The procedural sheath includes one or more channels extending longitudinally along a working length of the body of the sheath. Each channel includes one or more fluid paths configured to allow blood to flow from the vascular conduit into a device receiving lumen of the sheath. One or more elongate members selectively coupled to the body operatively cooperate with the channels to fluidly control fluid access into the device receiving lumen through the fluid paths.

30 Claims, 16 Drawing Sheets

A-A

(56) References Cited

U.S. PATENT DOCUMENTS

| | | |
|---|---|---|
| 7,503,893 B2 | 3/2009 | Kucklick |
| 7,575,565 B2 * | 8/2009 | Kucklick ............... A61B 1/015 |
| | | 604/35 |
| 7,722,558 B2 | 5/2010 | Ott |
| 7,892,203 B2 | 2/2011 | Lenker et al. |
| 8,545,481 B2 * | 10/2013 | Spehalski ......... A61M 25/0133 |
| | | 604/319 |
| 8,574,218 B2 * | 11/2013 | O'Day .............. A61M 25/0021 |
| | | 604/27 |
| 2003/0078539 A1 | 4/2003 | Peterson et al. |
| 2006/0253102 A1 | 11/2006 | Nance et al. |
| 2007/0250053 A1 | 10/2007 | Fernald et al. |

\* cited by examiner

A-A

PROCEDURAL SHEATH

BACKGROUND OF THE INVENTION

1. The Field of the Invention

The present invention relates generally to a procedural sheath and methods of use. More particularly, the present invention relates to a procedural sheath that helps maintain a fluid path while the procedural sheath is positioned within a vascular conduit or lumen to aid with performance of diagnostic or therapeutic procedures.

2. The Relevant Technology

A variety of sheaths and catheters are known in the art for treating the luminal system of a patient. Of such sheaths and catheters, many are directed to treating the cardiovascular system of a patient.

For example, as part of a diagnostic or therapeutic procedure, guidewires are inserted into a patient's vasculature through another catheter or sheath, such as an introducer. Following guidewire placement, medical professionals, such as physicians, clinicians, etc., advance other procedural devices such as catheters. occlusion devices, scaffolds, additional sheaths. or other diagnostic or therapeutic devices to a treatment region, in order to accommodate such devices, a catheter or sheath must have a sufficiently large bore through which the device can be passed.

However, during certain intravascular procedures, maintaining a large-bore sheath within the vasculature can lead to complications due to large-bore sheaths necessarily having larger outer diameters than. for example, small-bore sheaths that cannot accommodate the devices mentioned above. The large diameters of large-bore sheaths may present a greater risk of blocking blood flow through the vasculature in which the sheath is placed. For example, inserting a large-bore sheath into the femoral artery of a patient and towards the heart may block blood flow to the lower limbs. This blockage can lead to ischemia in the lower limb tissue of a patient due to a lack of oxygen being delivered to the tissue. Ischemia can cause pain or, in more critical cases, tissue loss.

The likelihood of these complications arising increases as the size of the vasculature decreases and as the duration of the procedure increases. For example, a patient may be at more risk of ischemia when a large-bore sheath is inserted at a site anterior to the knee and extended through the vasculature of the patient towards the ankle or foot, where the size of the vasculature decreases.

Also, procedures that require a large-bore sheath to be inserted in the vasculature for an extended period of time increases the risk of tissue loss due to ischemia, as the tissue may be lacking sufficient oxygen for a long period of time. Extended procedures such as these may include the use of embolic devices to occlude aneurysms, implanting scaffolds, stent delivery, or the like.

Accordingly, there exists a need for large-bore sheath systems, methods, and apparatus that can accommodate a number of procedural devices within the sheath without significantly blocking blood flow through the vasculature of a patient.

BRIEF SUMMARY OF THE INVENTION

The present invention relates generally to a procedural sheath and methods of use. More particularly, the present invention relates to a procedural sheath that helps maintain a fluid path while the procedural sheath is positioned within a vascular conduit or lumen to aid with performance of diagnostic or therapeutic procedures. For example, in one embodiment, a procedural sheath includes a body comprising one or more channels and one or more fluid paths formed in a base of each channel. Each of the fluid paths may include an inlet in the base of the channel and an outlet at a device receiving lumen of the body. The device receiving lumen is generally uniform in diameter along the length of the body.

In one embodiment, a procedural sheath includes an elongate member selectively coupled to the body. The elongate member cooperates with the channel and fluidly controls fluid access into the device receiving lumen by selectively closing the inlets of the fluid paths within the channel.

In one embodiment, according to the present disclosure, a large-bore procedural sheath includes a body that has a proximal end, a distal end, and a length extending therebetween. Also, a plurality of channels extend on the surface of the body and longitudinally for at least about 70% of the length. In one embodiment, the large-bore sheath includes a device receiving lumen that has a substantially uniform diameter along the length of the lumen from the proximal end to the distal end of the body. The lumen is configured to receive a procedural device therein. Also, in one embodiment according to the present disclosure, the large-bore procedural sheath includes a plurality of fluid paths formed in each channel. In one embodiment, each fluid path includes an inlet at the channel and an outlet at the device receiving lumen so that the device receiving lumen is in fluid communication with the channel through the fluid paths.

In one embodiment according to the present disclosure, the procedural sheath includes an elongate body and a hub coupled to the proximal end of the body. The hub is configured to selectively move an elongate member between a first configuration and a second configuration. In one embodiment, the first configuration includes a plurality of elongate members received into a plurality of channels and the second configuration includes the plurality of elongate members extending radially outwardly from the elongate body of the procedural sheath. In one embodiment, in the second configuration, a plurality of fluid paths formed in the channels are uncovered to allow fluid communication between a lumen of the sheath and the channels. Also, in the second configuration, the outwardly extending elongate members exert a force against an interior surface of the wall of a vasculature in which the sheath is disposed.

In one embodiment according to the present disclosure, a method for performing an intravascular procedure while maintaining a fluid path through a vascular conduit of a patient includes a first step of providing a procedural sheath according to the present disclosure. In one embodiment of the method, a further step includes advancing the procedural sheath into a vascular conduit of a patient. One embodiment of the method also includes moving the elongate member radially outwardly from the body to push radially outwardly on an inside surface of the conduit and allow fluid access into the device receiving lumen of the body. One embodiment of the method also includes advancing a procedural device into the device receiving lumen of the body.

These and other objects and features of the present invention will become more fully apparent from the following description and appended claims or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
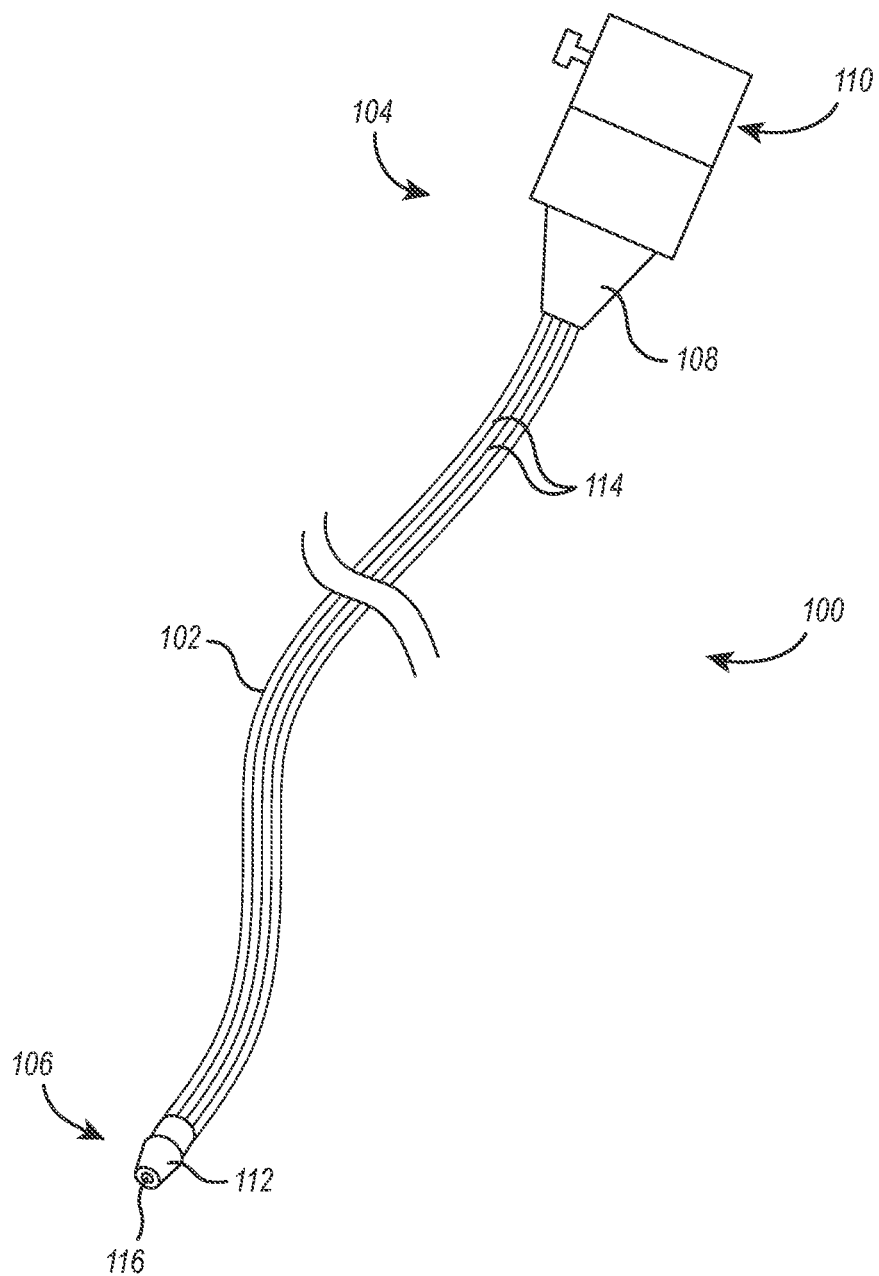
FIG. 1 illustrates a procedural sheath according to an embodiment of the present disclosure.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more of the embodiments of the present disclosure may generally relate to a procedural sheath and methods of use. More particularly, the present invention relates to a procedural sheath that helps maintain a fluid path while the procedural sheath is positioned within a vascular conduit or lumen to aid with performance of diagnostic or therapeutic procedures. For example, in one embodiment, a procedural sheath includes a body comprising one or more channels and one or more fluid paths formed in a base of each channel. Each of the fluid paths may include an inlet in the base of the channel and an outlet at a device receiving lumen of the body. The device receiving lumen is generally uniform in diameter along the length of the body.

In one embodiment, a procedural sheath includes an elongate member selectively coupled to the body. The elongate member cooperates with the channel and fluidly controls fluid access into the device receiving lumen by selectively closing the inlets of the fluid paths within the channel.

In one embodiment, according to the present disclosure, a large-bore procedural sheath includes a body that has a proximal end, a distal end, and a length extending therebetween. Also, a plurality of channels extend on the surface of the body and longitudinally for at least about 70% of the length. In one embodiment, the large-bore sheath includes a device receiving lumen that has a substantially uniform diameter along the length of the lumen from the proximal end to the distal end of the body. The lumen is configured to receive a procedural device therein. Also, in one embodiment according to the present disclosure, the large-bore procedural sheath includes a plurality of fluid paths formed in each channel. In one embodiment, each fluid path includes an inlet at the channel and an outlet at the device receiving lumen so that the device receiving lumen is in fluid communication with the channel through the fluid paths.

In one embodiment according to the present disclosure, the procedural sheath includes an elongate body and a hub coupled to the proximal end of the body. The hub is configured to selectively move an elongate member between a first configuration and a second configuration. In one embodiment, the first configuration includes a plurality of elongate members received into a plurality of channels and the second configuration includes the plurality of elongate members extending radially outwardly from the elongate body of the procedural sheath. In one embodiment, in the second configuration, a plurality of fluid paths formed in the channels are uncovered to allow fluid communication between a lumen of the sheath and the channels. Also, in the second configuration, the outwardly extending elongate members exert a force against an interior surface of the wall of a vasculature in which the sheath is disposed.

In one embodiment according to the present disclosure, a method for performing an intravascular procedure while maintaining a fluid path through a vascular conduit of a patient includes a first step of providing a procedural sheath according to the present disclosure. In one embodiment of the method, a further step includes advancing the procedural sheath into a vascular conduit of a patient. One embodiment of the method also includes moving the elongate member radially outwardly from the body to push radially outwardly on an inside surface of the conduit and allow fluid access into the device receiving lumen of the body. One embodiment of the method also includes advancing a procedural device into the device receiving lumen of the body.

The procedural sheath of the present disclosure may enable medical professionals, such as physicians, clinicians, etc., to reduce the risk of ischemia and other complications while performing intravascular procedures. The procedural sheath of the present disclosure may provide a device receiving lumen large enough to accommodate a variety of procedural devices without significantly blocking blood flow through the vasculature in which the sheath is placed. As a result, the sheath may reduce pain and tissue damage in patients undergoing procedures that require access through small-diameter vasculature and/or procedures that require intravascular access for extended periods of time.

Turning now to the figures, FIG. 1 illustrates a procedural sheath 100 according to an embodiment of the present disclosure. The illustrated sheath 100 includes an elongate body 102 extending from a proximal end 104 to a distal end 106. In one embodiment, the sheath 100 may have a length extending between the proximal end 104 and the distal end 106 of between about 25 cm and 120 cm. In another embodiment, the length may be between about 40 cm and 110 cm. In yet another embodiment, the length may be between about 55 cm and 100 cm. Additionally, one or more embodiments of the sheath 100 may have a length between the distal and 106 and the proximal end 104 of about 65 cm, 70 cm, 85 cm, or 90 cm. The sheath 100 may also include a stress relief feature 108 and a hub 110 disposed at the proximal end 104 thereof. In addition, the sheath 100 may include a tip 112 disposed at the distal end 106. One or more channels 114 may extend longitudinally along a substantial portion of the working length of the body 102.

In addition to the features of the sheath 100 mentioned above, the sheath 100 may also include an interior device receiving lumen configured to receive a procedural device. The device receiving lumen (not illustrated in FIG. 1) may extend from the proximal end 104 to the distal end 106 of the sheath 100. The device receiving lumen may be configured so that a procedural device, such as, for example, an embolic coil or guidewire, may be inserted proximally through the hub 110 and into the sheath 100. The procedural device may be advanced through the device receiving lumen to the distal end 106 of the sheath 100 and out an opening 116 in the tip 116, as may be required for certain procedures.

The body 102 of the sheath may be made of various bio-compatible materials that maintain proper flexibility for navigating the vasculature of a patient as well as proper elasticity and/or stiffness to prevent kinking. Such materials, which may be well known in the art, may include, but are not limited to, Polyethylene, Fluorinated Ethylene Propylene, or other Fluoropolymers. In addition, these materials may be coated with lubricious coatings, either hydrophilic or hydrophobic. Strong and lubricious materials are preferred. The body 102 may be extruded or otherwise formed using methods that are generally known in the art.

The stress relief feature 108 of the sheath 100 may also be made of similar materials. The stress relief feature 108 may be more or less stiff than the body 102 and shaped so as to relieve/distribute stress concentrations that may occur at the proximal end 104 of the body 102, where the body 102 and hub 110 meet. The stress relief feature 108 may be molded or otherwise formed with the body 102 and include an inner lumen (not shown) for passing a procedural device through the hub 110 and into the device receiving lumen of the body 102.

As noted above, the sheath 100 may include a tip 112 disposed at the distal end 106 of the body 102. The tip 112 may be made of a more rigid material than that of the body 102 and include an opening 116 through which a procedural device may pass. The tip 112 preferably may comprise a radiopaque material that can be imaged from outside the body to assist a physician or other medical professional in locating and properly positioning the sheath 100 within the vasculature of a patient as required by a procedure. For example, the tip 112 may comprise materials such as steel, stainless steel, cobalt-chromium, titanium, Nitinol, or any number of polymers loaded with metal such as barium sulfate, Bismuth, Tungsten, and the like.

The tip 112 may also provide a portion of the body 102 that more reliably maintains its shape and opening 116 to ensure access to the vasculature from the device receiving lumen inside the body 102 of the sheath. The tip 112 may be extruded or molded together with the body 102, molded separately and then molded or adhered to the body 102, or otherwise permanently disposed at the distal end 106 thereof.

FIG. 1 also illustrates one or more channels 114 extending longitudinally along the outer surface of the body 102. In the illustrated embodiment, the channels may run substantially parallel to one another and be spaced around the circumference of the body 102. The number and configuration of the channels 114 may vary in different embodiments. For example, in one embodiment, the body 102 of the sheath 100 may include 4 channels 114 spaced around the body 102 and extending longitudinally from the proximal end 104 to the distal end 106. In one embodiment, the body 102 may include 3 channels 114, or less than 3 channels. In yet another embodiment, the body 102 may include between 4 and 8 channels 114. In yet another embodiment, the body 102 may include more than 8 channels 114 extending longitudinally thereon.

In the various embodiments of the sheath 100 described herein, the channels 114 may extend longitudinally along a substantial portion of working length of the body 102. For example, the channels 114 may extend along at least about 70% of the working length of the body 102. In one embodiment, the channels 114 may extend along at least about 80% of the working length of the body 102. In yet another implementation, the channels 114 may extend between 85% and 95% along the working length of the body 102. For example, in one embodiment, the channels 114 may extend 90% along the working length of the body 102 of the sheath 100. The channels 114 may terminate at the tip 112 disposed at the distal end 106 and about 10 cm distal to the strain relief feature 108 at the proximal end 104.

Figure 2A:
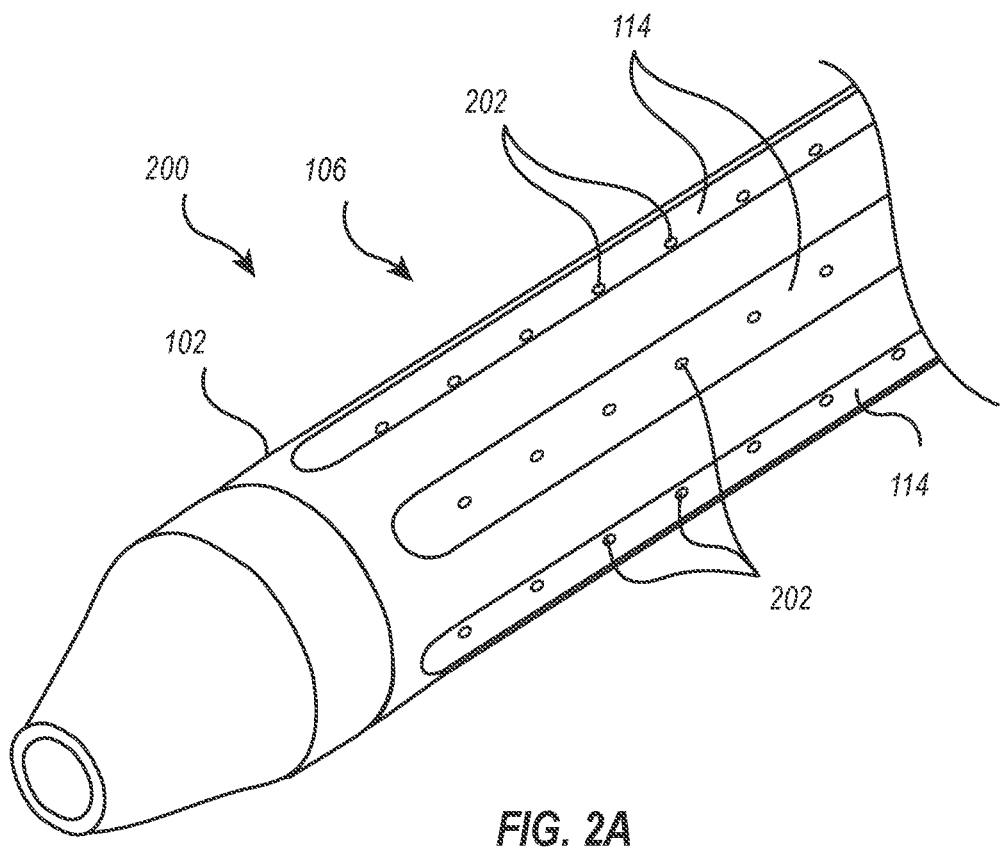
FIG. 2A illustrates a perspective view of the distal end of a procedural sheath according to an embodiment of the present disclosure.
Figure 2B:
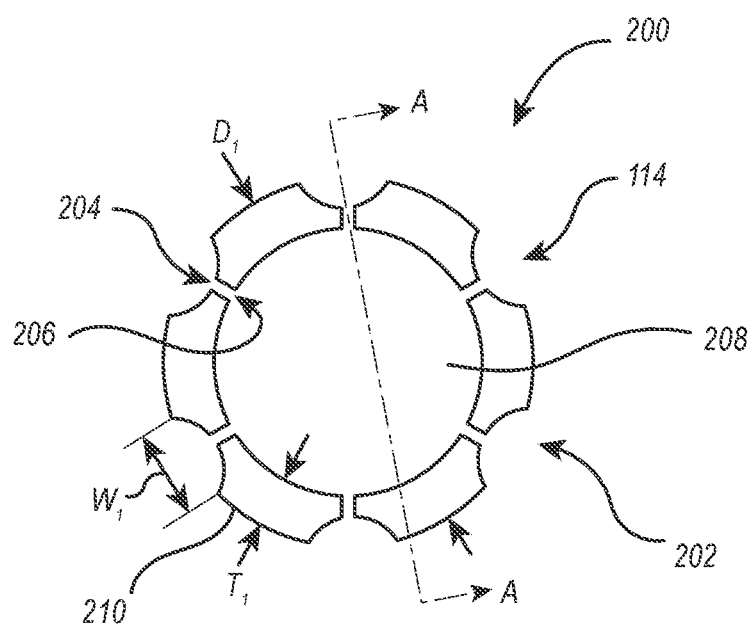
FIG. 2B illustrates a transverse cross-sectional view thereof.

FIG. 2A shows a close-up view of the distal end 106 of an embodiment of a sheath 200 having a plurality of channels 114 extending longitudinally along the working length of the body 102. In the illustrated embodiment, each of the channels 114 may include one or more fluid paths 202 formed in each channel 114. FIG. 2B illustrates a transverse cross-sectional view of the body 102 illustrated in FIG. 2A. As shown in FIG. 2B, each fluid path 202 may include an inlet 204 formed at the channel 114 and an outlet 206 formed at a device receiving lumen 208 extending through an interior of the body 102. In one implementation, each fluid path 202 may be formed as a perforation extending between an inlet 204 and outlet 206. Fluid, such blood flowing through the vasculature of a patient, may pass through the fluid path 202 from outside the body 102 of the sheath into the device receiving lumen 208.

FIG. 2B also illustrates cross-sectional views of the channels 114 spaced around the body 102 of the sheath 100. In the illustrated embodiment, the body 102 includes 6 channels 114 spaced evenly around the circumference thereof. However, as discussed above, the number and spacing of the channels may vary in different embodiments. As shown in the illustrated embodiment, the channels 114 consist of semi-circular cutouts of material forming portions of the body 102 that are recessed from the outer surface of the body 102. In one or more other embodiment, the channels 114 may have cross-sectional shapes other than semi-circular. For example, in one or more embodiments, the cross-sectional shape of each channel may be rectangular, triangular, or otherwise polygonal in shape.

The cross-sectional view of the body 102 illustrated in FIG. 2B also shows a body wall 210 defined by material between an outer surface of the body 102 and the device receiving lumen 208. Because the channels 114 may comprise material removed from the wall 210, the thickness of the wall 210 may vary around the circumference of the body 102. For example, a portion of the wall 210 that does not include a channel 114 may be thicker than a portion of the wall 210 that does include a channel 114. Thus, the thinnest portion of the wall 210 may be where the lowest point, or base, of a channel 114 is disposed. In one embodiment, a thickness T1 of the wall 210, at a point where no channel resides, may be between about 0.05 inches and 0.1 inches. In another embodiment, the thickness T1 of the wall 210 may be between about 0.04 and 1.2 inches. In yet one or more other embodiments, the thickness T1 of the wall 210 may be between about 0.02 inches and 0.03 inches.

As shown in the illustrated embodiment of FIG. 2B, each fluid path 202 may be disposed through the thinnest portion of the wall 210. In other words, each inlet 204 of each fluid path 202 may be disposed at the base of each of the channels 114. In one embodiment, each channel may have a depth of between about 0.04 inches and 0.9 inches. In another embodiment, each channel may have a depth ranging between about 0.03 inches and 1.1 inches. In any case, the depth of each channel 114 is preferably less than the thickness of the wall 210 so that channels 114 do not extend all the way through the wall 210. Also, each channel may have a width W1 at the surface of the body 102 of less than about 0.1 inches.

FIG. 2B also illustrates an outer diameter of the body D1 and a diameter D2 of the device receiving lumen 208. In one embodiment, the outer diameter D1 may be between about 0.36 inches and 0.47 inches. In another embodiment, outer diameter D1 may be between about 0.35 inches and 0.49 inches. In any case, the outer diameter of the body 102 is equal to the diameter of the device receiving lumen 208 plus the wall thickness T1. In one embodiment, the diameter D2 of the device receiving lumen 208 may be between about 0.31 inches and 0.37 inches. In one embodiment, the diameter D2 may be between about 0.33 inches and 0.35 inches. For example, in one embodiment, the diameter D2 may be 0.34 inches. Also, for example, in another embodiment, the diameter D2 may be 0.32 inches or 0.36 inches. Preferably, the diameter D2 of the device receiving lumen 208 may be such that a 24-French procedural device can be inserted and advanced therethrough.

Figure 2C:
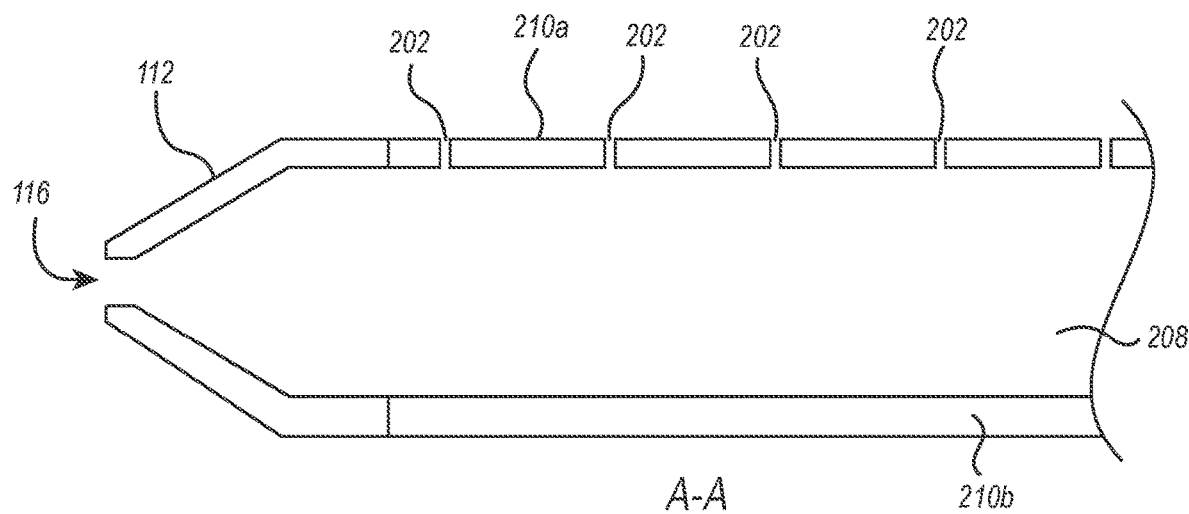
FIG. 2C illustrates a longitudinal cross-sectional view thereof.

FIG. 2C illustrates another cross-sectional view of the sheath 200 illustrated in FIG. 2A. The cross-section view of FIG. 2C is taken through the plane denoted as A-A in FIG. 2C. As seen in FIGS. 2B and 2C, the device receiving lumen has a circular cross-sectional area that extends longitudinally along the length of the body 102. The diameter D2 of the device receiving lumen 208 may be substantially uniform along the length of the body 102 to the tip 112, as well as radially uniform around the cross-sectional diameter D2, shown in FIG. 2B. The uniformity of the device receiving lumen 208 may provide a smooth, unobstructed path through which a procedural device may be advanced.

FIG. 2C also illustrates a cross-sectional view of the wall 210 of the body 102 taken through plane A-A, as denoted in FIG. 2B. The upper wall 210*a* of FIG. 2C is thinner than the bottom wall 210*b* due to the plane A-A crossing through a channel 114 at the top and not at the bottom. Thus, fluid channels 202 are visible in the top wall portion 210*a* and not in the bottom wall portion 210*b*.

Figure 3A:
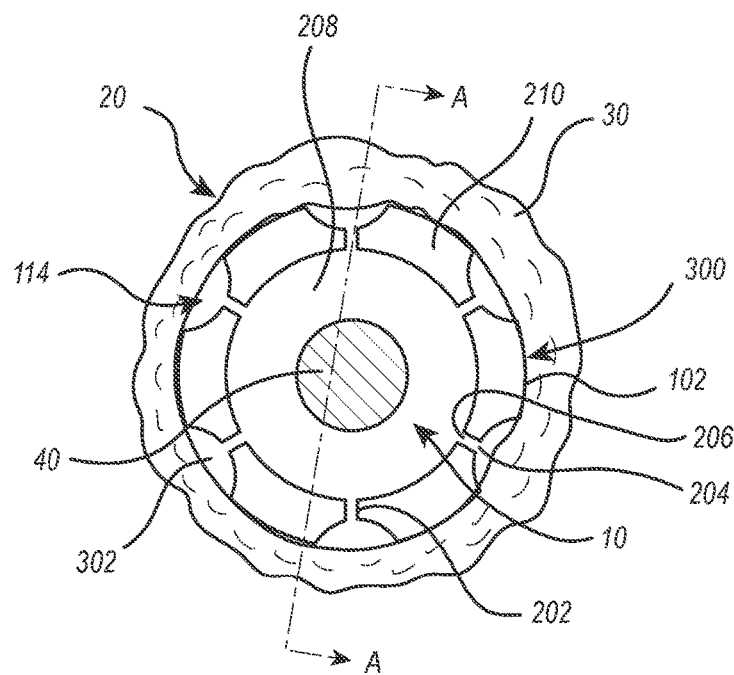
FIG. 3A illustrates a transverse cross-sectional view of a procedural sheath inserted into the vasculature of a patient according to an embodiment of the present disclosure.
Figure 3B:
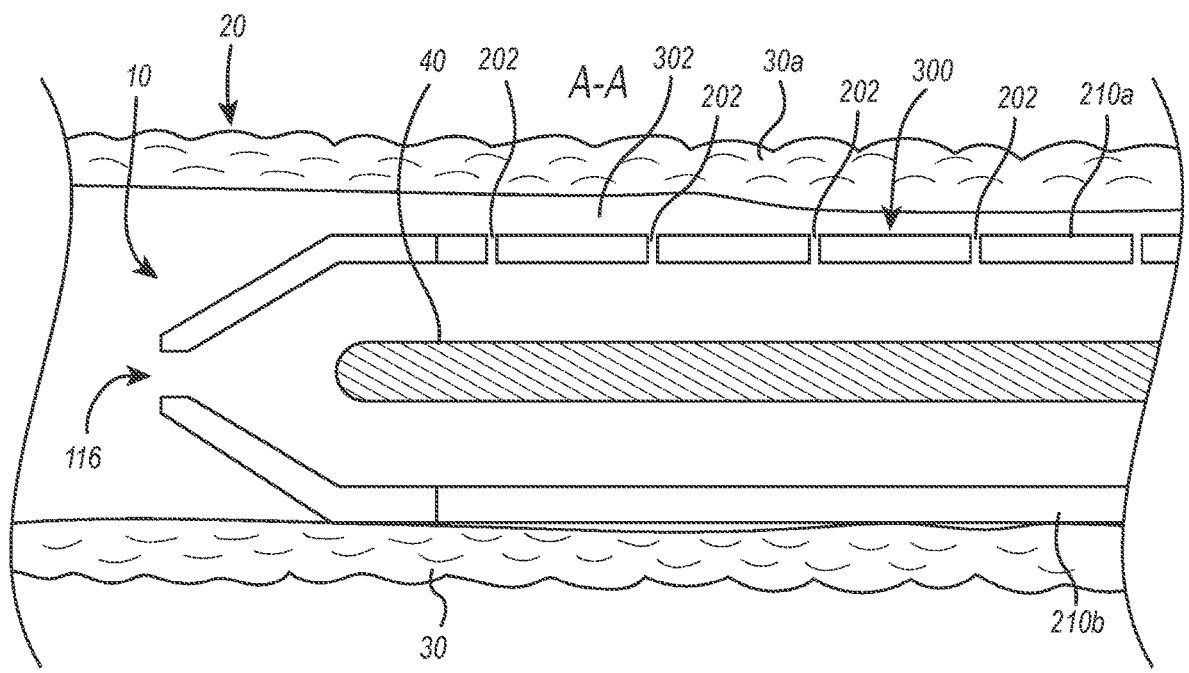
FIG. 3B illustrates a longitudinal cross-sectional view thereof.

Likewise, FIG. 3B is a cross-sectional view of an embodiment of a sheath 300 taken through plane A-A, as denoted in FIG. 3A. FIG. 3A is a cross-sectional view of a sheath 300 similar to the sheath 200 illustrated in FIG. 2B, but where the sheath 300 is disposed within a conduit of the vasculature of a patient. Referring first to FIG. 3A, the sheath 300 may be disposed so that the wall 210 of the body 102 presses against the vascular wall 30. FIG. 3A further illustrates a space 302 created between the wall 210 of the body 102 and the vasculature wall 30. The inlet 204 of each fluid path 202 may therefore be disposed at the space 302 provided by the channels 114. Thus, fluid, such as blood within the conduit 10 of a patient's vasculature 20 residing in the spaces 302, may enter into the device receiving lumen 208 through the various fluid paths 202. Once the blood enters the device receiving lumen 208, the blood may continue to be pumped through the vascular conduit 10, carrying oxygen to the tissue of the patient as needed.

It is noted, for clarification with reference to FIG. 3B, that the spaces 302 are visible between the upper sheath wall 210*a* and vascular wall 30*a* but not between lower sheath wall 210*b* and vascular wall 30*b*. This is because the viewing plane of FIG. 3B is taken through the cross-sectional plane A-A, as denoted in FIG. 3A. This plane A-A passes through a channel 114 at the top wall 210*a* and not through a channel 114 at the bottom wall 210*b*. Thus, the wall 210 may press against the vascular wall 30 around the circumference of the body 102, except at the spaces 302 provided by the channels 114. As such, the view illustrated in FIG. 3B shows the bottom wall 210*b* close to, or in contact with, the vascular wall 30*b* and a space 302 provided between the upper sheath wall 210*a* and vascular wall 30*a*.

It is also noted that the material and wall thickness T1 of the body 102 may be configured such that forces exerted radially inwardly onto the sheath 300 by the vasculature 20 are insufficient to collapse the body 102. For example, in one embodiment, the wall 210 maintains a radial force transferred from the elongate members 402 to the body 102 of between about 1 Newton and 7 Newtons. In another embodiment, the wall 210 maintains a radial force of between about 0.5 to 10 Newtons. As such, the sheath 300 may maintain an open device receiving lumen 208 through which blood or other fluid may pass when the sheath 300 is advanced through the vasculature of a patient.

FIGS. 3A and 3B further illustrate a procedural device 40 that has been advanced through the device receiving lumen 208 of the sheath 300. As discussed above, the sheath 300 may be a large bore sheath configured to accommodate a procedural device of at least about 24-French. The procedural device 40 may be advanced from the proximal end 104 of the sheath 300, through the device receiving lumen 208 to the distal end 106, and additionally through the opening 116 in the tip 112. Thus, a physician or other medical professional may be able to perform various therapeutic, corrective, implantation, or other intravascular procedures through the sheath 300 without significantly blocking blood flow through the vasculature 20 in which the sheath 300 is advanced.

Figure 4A:
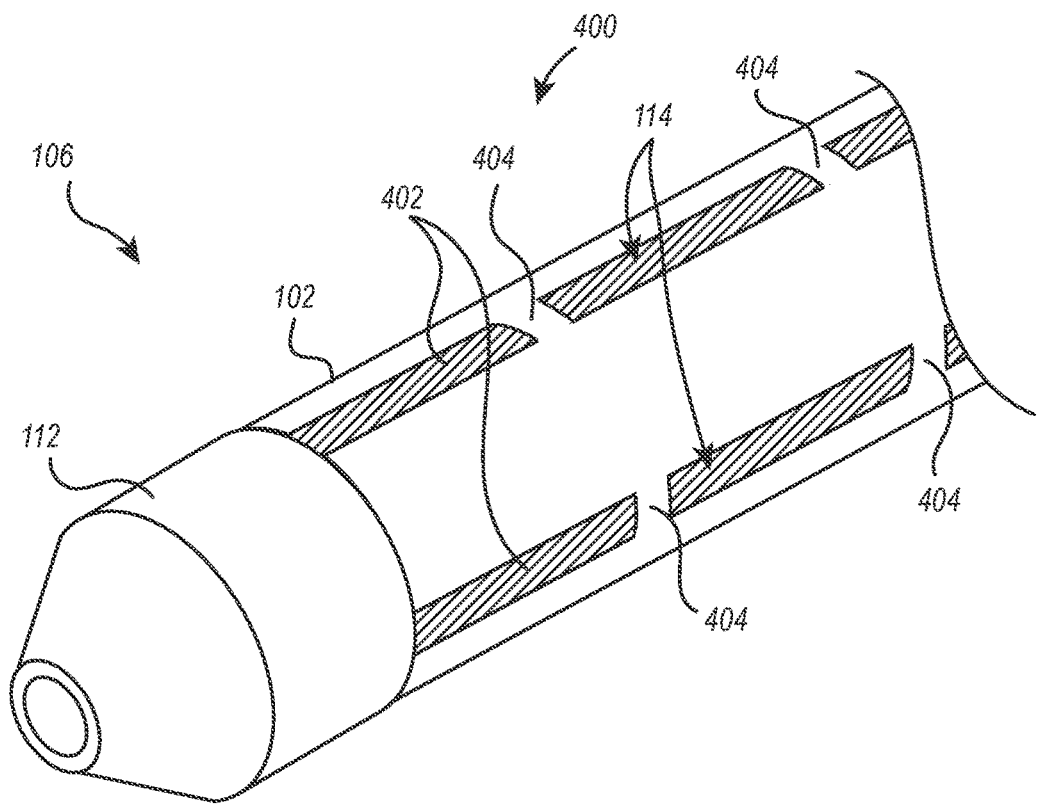
FIG. 4A illustrates a perspective view of the distal end of a procedural sheath according to an embodiment of the present disclosure.
Figure 4B:
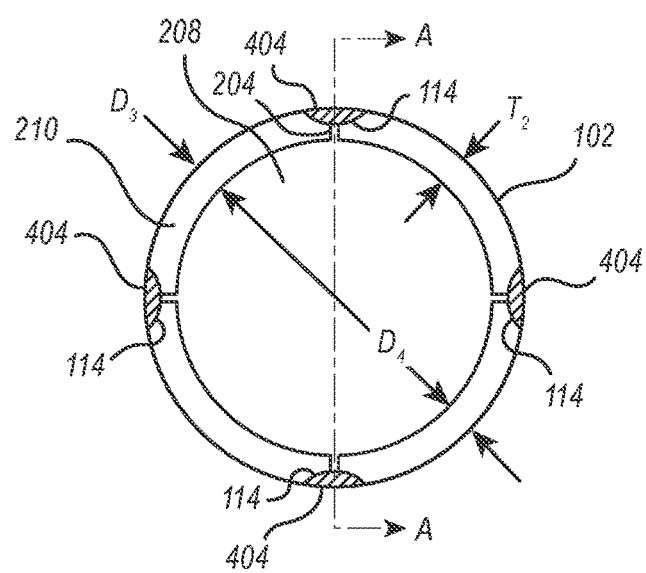
FIG. 4B illustrates a transverse cross-sectional view thereof.
Figure 4C:
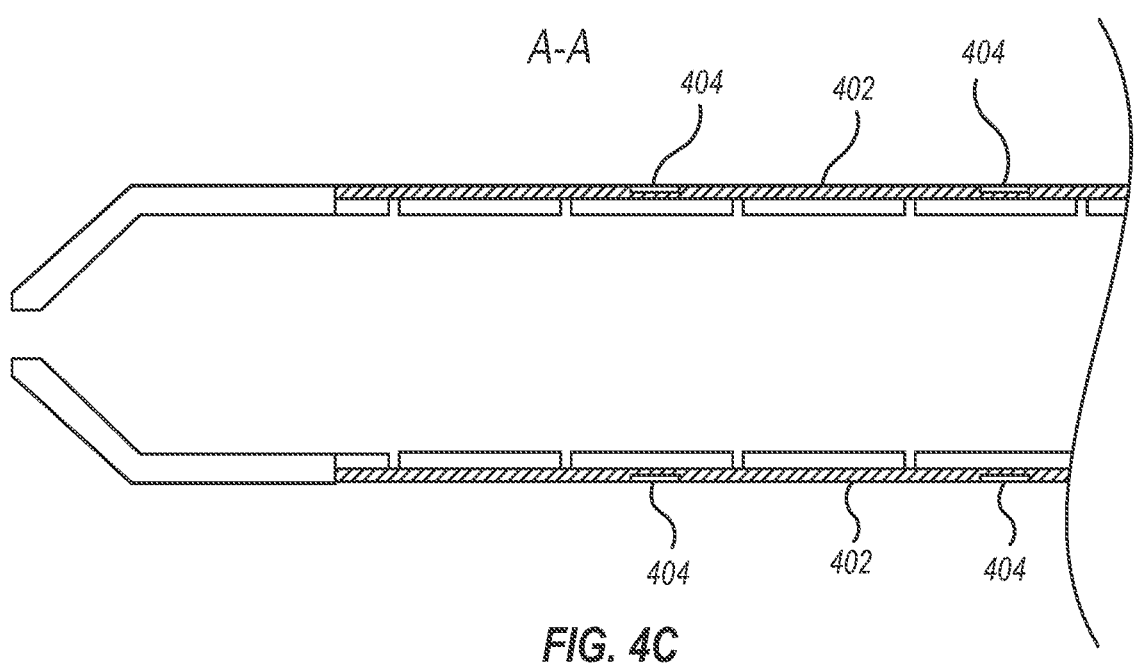
FIG. 4C illustrates a longitudinal cross-sectional view thereof.

Turning now to FIGS. 4A through 4C, another embodiment of a sheath 400 is illustrated. In particular, FIG. 4A illustrates a perspective view of the distal end 106 of the sheath 400, while FIGS. 4B and 4C illustrate various cross-sectional views thereof. As shown by FIG. 4A, the sheath 400 may include a body 102, tip 112, and one or more channels 114. Additionally, the sheath 400 may include one or more elongate members 402 selectively coupled to the body 102 and extending longitudinally along the body 102, cooperating with the channels 114.

For example, as shown in the transverse cross-section view of FIG. 4B, the elongate members 402 may be disposed within the channels 114 so that the elongate members 402 do not extend beyond the outer diameter D2 of the body 102. Furthermore, in one embodiment, the elongate members 402 may be shaped such that the elongate members 402 coincide in shape with the channels 114 and block off the inlets 204 of the fluid paths 202. The illustrated embodiment of FIGS. 4A through 4C includes 4 channels 114 spaced about the circumference of the body 102 with 4 elongate members 402 disposed therein. As noted above, other embodiments may include more or less than 4 channels 114. Also, as discussed above, the dimensions, configurations, and shape of the wall 210, channels 114, fluid paths 202, and device receiving lumen 208 may be similar to other embodiments described herein.

For example, in one embodiment, the outer diameter D3 may be between about 0.36 inches and 0.47 inches. In another embodiment, outer diameter D3 may be between about 0.35 inches and 0.49 inches. In any case, the outer diameter of the body 102 is equal to the diameter of the device receiving lumen 208 plus the wall thickness T2. In one embodiment, the diameter D4 of the device receiving lumen 208 may be between about 0.31 inches and 0.37 inches. In one embodiment, the diameter D4 may be between about 0.33 inches and 0.35 inches. For example, in one embodiment, the diameter D4 may be 0.34 inches. Also, for example, in another embodiment, the diameter D4 may be 0.32 inches or 0.36 inches. Preferably, the diameter D4 of the device receiving lumen 208 may be such that a 24-French procedural device can be inserted and advanced therethrough.

The elongate members 402 illustrated in FIGS. 4A through 4C may extend longitudinally along the working length of the body 102 of the sheath 400 along with the channels 114 as described herein. Thus, the elongate members 402 may extend along at least about 70% of the working length of the body 102. In one embodiment, the elongate members 402 may extend along at least about 80% of the working length of the body 102. In yet another implementation, the elongate members 402 may extend between 85% and 95% along the working length of the body 102. For example, in one embodiment, the elongate members 402 may extend 90% along the working length of the body 102 of the sheath 100. The elongate members 402 may terminate at the tip 112 disposed at the distal end 106 and about 10 cm distal to the strain relief feature 108 at the proximal end 104.

In addition to the elongate members 402 illustrated in FIGS. 4A through 4C, FIGS. 4A and 4C also illustrate one or more support regions 404 dispersed along the length of the elongate members 402. In one embodiment, the support regions 404 may overlap the elongate members 402 and restrict the outward radial movement of the elongate members 402 away from the body 102. For example, as seen in the cross-sectional view of FIG. 4C, one or more support regions 404 are disposed radially outward form the elongate members 404. Thus, in one or more embodiments, the elongate members 402 may be disposed within the channels 114 and below the support regions 404.

The support regions 404 may be formed integrally with the material of the body 102 or separately formed and molded, or otherwise adhered, to the body 102 so that the support regions 404 span the channels 114 over the elongate members 404. The number and distance between adjacent support regions 404 may vary. Also, the thickness and strength of the support members 404 are preferably sufficient to restrain at least portions of the elongate members 402 within the channels 114. The thickness, length, and width of the support regions 404 may vary in different embodiments.

Figure 5A:
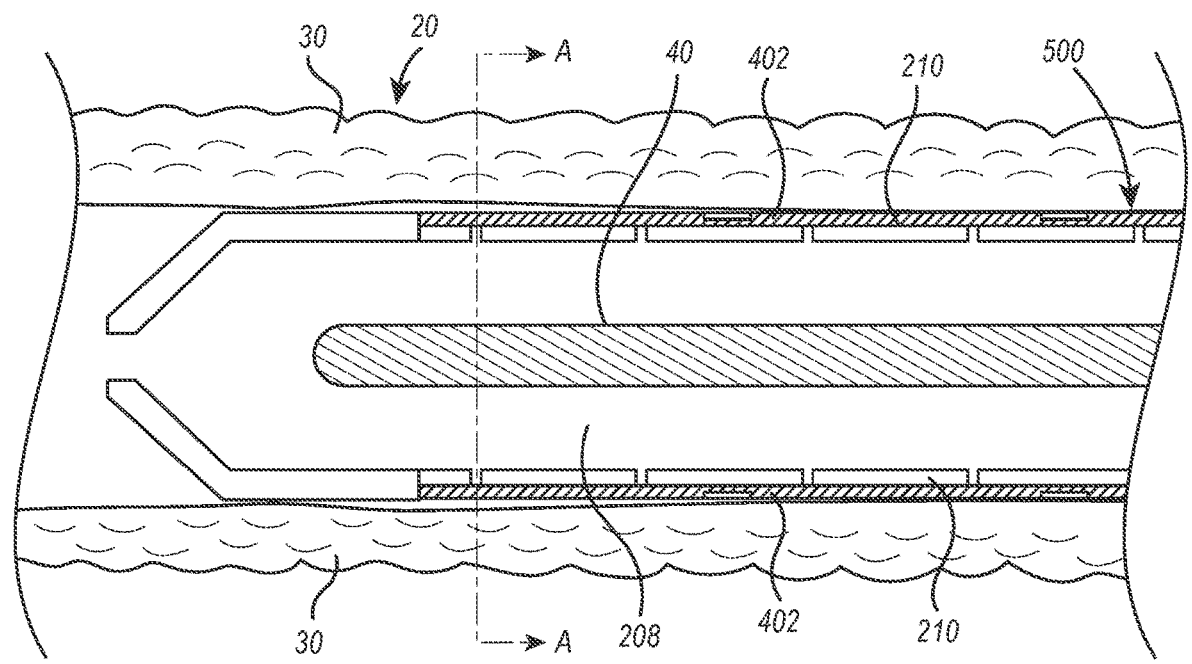
FIG. 5A illustrates a longitudinal cross-sectional view of a procedural sheath inserted into the vasculature of a patient according to an embodiment of the present disclosure.
Figure 5B:
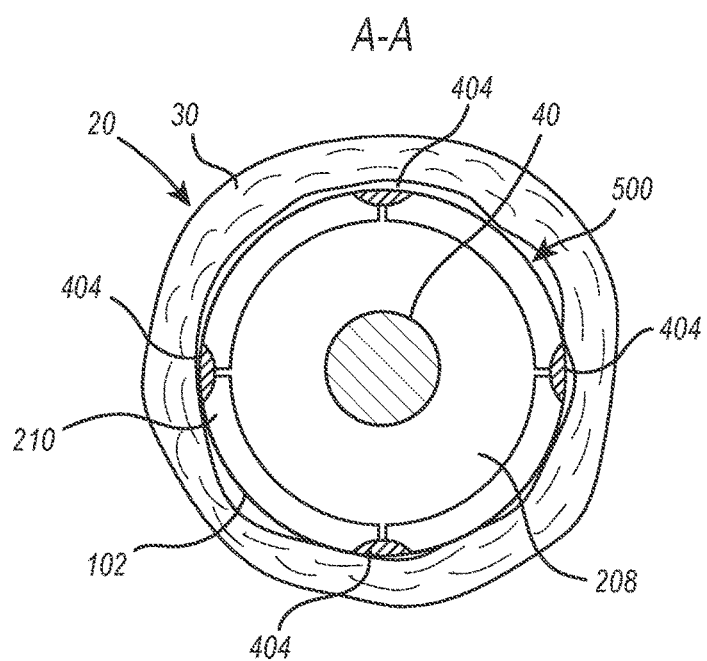
FIG. 5B illustrates a transverse cross-sectional view thereof.

FIGS. 5A and 5B illustrate cross-sectional views of an embodiment of a sheath 500 similar to the embodiment illustrated in FIG. 4A. However, in the illustrated embodiment, the sheath 500 has been advance into the vasculature 20 of a patient and a procedural device 40 has been advanced through the device receiving lumen 208. The outer diameter D3 of the sheath 500 is such that the wall 210 of the body 102 presses against or contacts the vascular wall 30 of the patient, similar to other embodiments described herein in reference to FIGS. 3A and 3B. However, in the embodiment of the sheath 500 illustrated in FIGS. 5A and 5B, little or no space is present between the wall 210 of the body 102 and the vascular wall 30 because the elongate members 402 are received within the channels 114 instead.

Figure 6A:
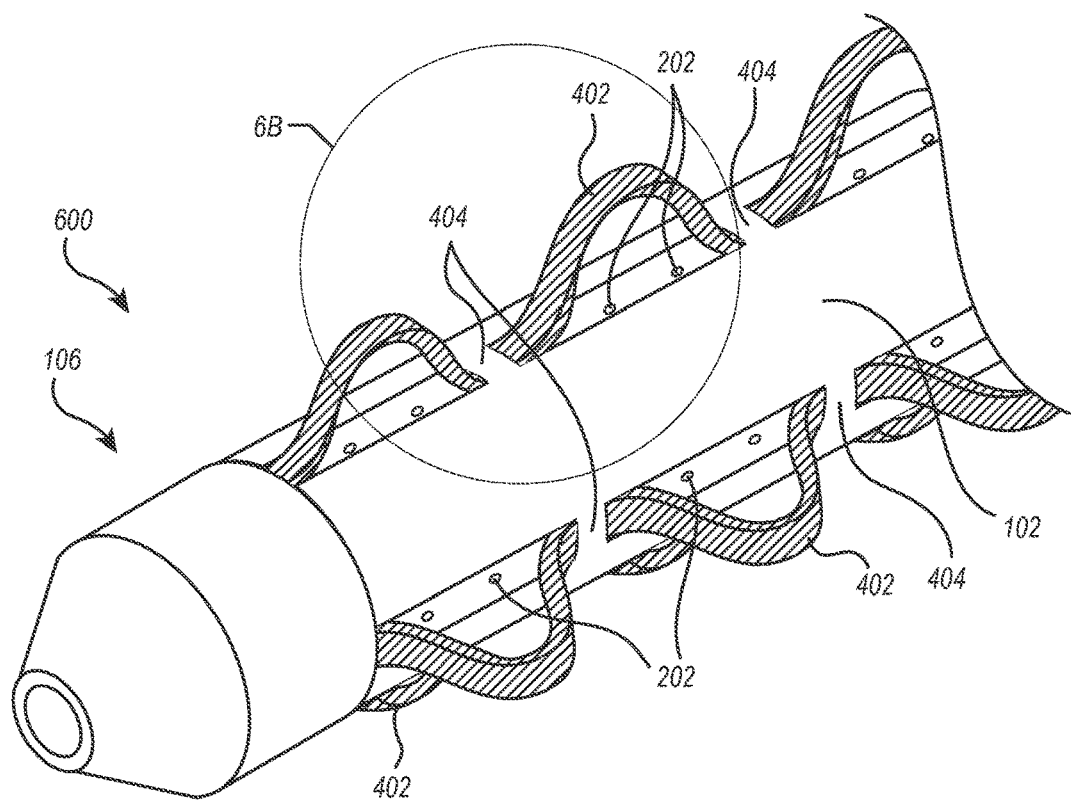
FIG. 6A illustrates a perspective view of the distal end of a procedural sheath according to an embodiment of the present disclosure.

Thus, in the configuration of the embodiments shown in FIGS. 4A through 5B, little or no blood flowing through the vasculature 20 of the patient may enter the device receiving lumen 208. However, the elongate members 402 may be selectively moved to extend radially outwardly from the body 102, as shown in FIGS. 6A through 7B. Along these lines, FIG. 6A illustrates a perspective view of the distal end 106 of a sheath 600, similar to the sheath 500 illustrated in FIGS. 4A through 5B, but where the elongate members 402 have been selectively moved radially outwardly from the body 102.

As shown in the embodiment of FIG. 5A, the fluid paths 202 may be exposed when the elongate members 402 are selectively moved radially outwardly from the body 102. In this configuration, at least portions of the elongate members 402 no longer cover the inlets 204 of the fluid paths 202. In one embodiment, two or three fluid paths 202 may be disposed within the channel 114 between each pair of adjacent support regions 404. In one or more embodiments, less than 3 or more than 4 fluid paths 202 may be disposed in the channels 114 between adjacent support regions 404.

The elongate members 402 described herein may be made of flexible, elastic, pseudoelastic or superelastic materials that enable portions of the elongate members 402 to be repeatedly bent outward, away from the body 102 of the sheath 600, and returned to a flat configuration where the elongate members 402 are received back into the channels 114. The material may also preferably be biocompatible material. Examples of such materials may include, but are not limited to, shape memory materials such as Nitinol, gold-cadmium, copper-zinc or other materials, including ferro-magnetic shape alloys.

Figure 6B:
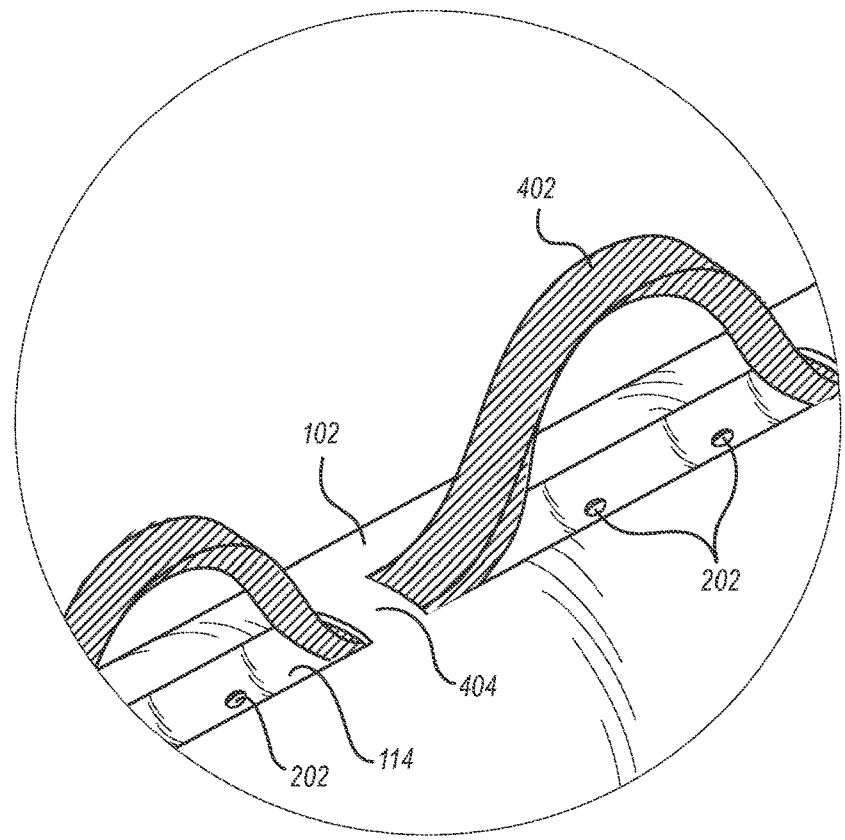
FIG. 6B illustrates a close-up perspective view thereof.

FIG. 6B illustrates a close-up view of the sheath 600 of FIG. 6A to clarify the interaction between the channel 114, elongate members 402, and support regions 404, when the elongate members 402 have been selectively moved to extend radially outwardly from the body 102. As shown in the embodiment of FIG. 6B, the support region 404 extends across the channel 114 and over the elongate member 402 to restrain the portion of the elongate member 404 disposed under the support region 404 from being extended away from the body 102. Portions of the elongate member that are not restrained by the support region 404 may be extended outward as shown.

Accordingly, as discussed above, the one or more fluid paths 202 disposed within the channel 114 between the support regions 404 are exposed to allow blood, or other fluid within the vasculature of the patient, to flow into the device receiving lumen 208 of the sheath 600. Also, in one embodiment, the support region 404 is preferably not rigidly attached or secured to the elongate member 402 so that the elongate member 402 may slide longitudinally relative to the support region 404.

Figure 6C:
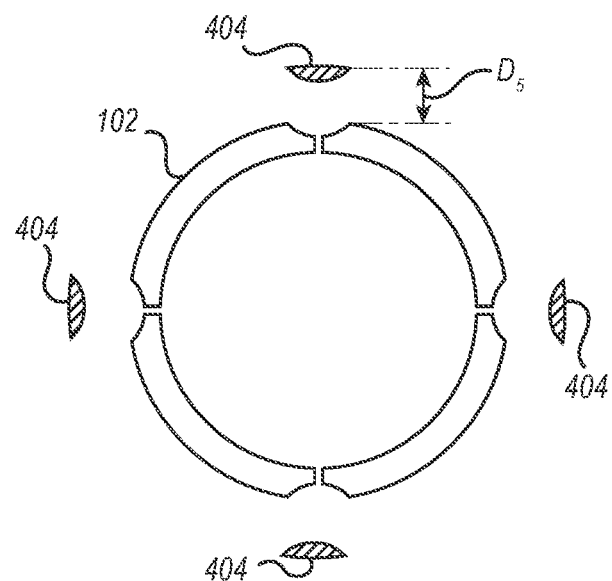
FIG. 6C illustrates a transverse cross-sectional view of the procedural sheath illustrated in FIGS. 6A and 6B.

FIG. 6C illustrates a transverse cross-sectional view of the sheath 600 of FIG. 6A. The cross-sectional plane of FIG. 6C is positioned along the longitudinal length of the body 102 where the elongate members 402 are extended outward between a pair of adjacent support regions 404. As shown in the embodiment of FIG. 6C, the elongate members 402 may extend radially outwardly from the body 102. In one embodiment, the elongate members 402 may selectively extend radially outwardly from the body 102 to distance D5 of between about 0.5 mm and 1.5 mm. In one or more other embodiments, the distance D5 may be between about 0.75 mm and 1.25 mm. In yet another embodiment, the distance D5 may be less than 0.5 mm or greater than 1.5 mm.

Figure 7A:
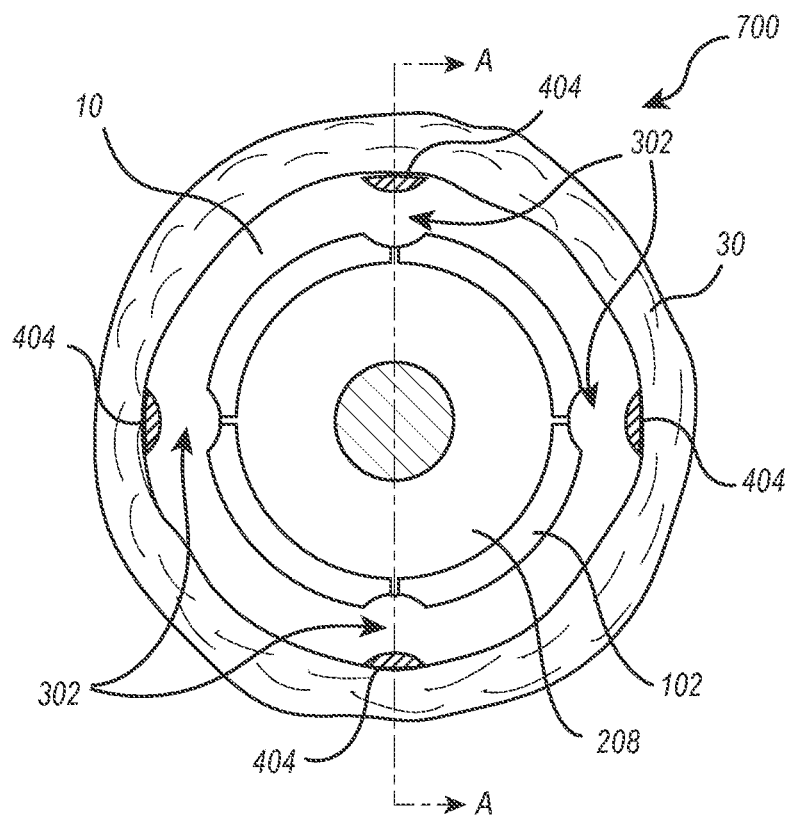
FIG. 7A illustrates a transverse cross-sectional view of a procedural sheath inserted into the vasculature of a patient according to an embodiment of the present disclosure.

FIG. 7A, similar to FIG. 6C, illustrates a transverse cross-sectional view of an embodiment of a sheath 700 similar to the sheath 600 shown in FIG. 6A. The sheath 700 of FIG. 7A has been inserted into a vascular conduit 10. The elongate members 402 have been selectively moved radially outwardly from the body 102 to push against the inside of the vascular wall 30. In one embodiment, the force of the extended elongate members 402 against the vascular wall 30 may expand the vascular wall 30 away from the body 102 to create spaces 302 where blood or other fluid within the vascular conduit 10 can enter the device receiving lumen 208 through the various fluid paths 202.

In this way, when the elongate members 402 are selectively moved radially outwardly from the body 102, fluid, such as blood within the conduit 10 of a patient's vasculature 20 residing in the spaces 302, may enter into the device receiving lumen 208 through the various fluid paths 202. Once the blood enters the device receiving lumen 208, the blood may continue to be pumped through the vascular conduit 10, carrying oxygen to the tissue of the patient as needed.

Figure 7B:
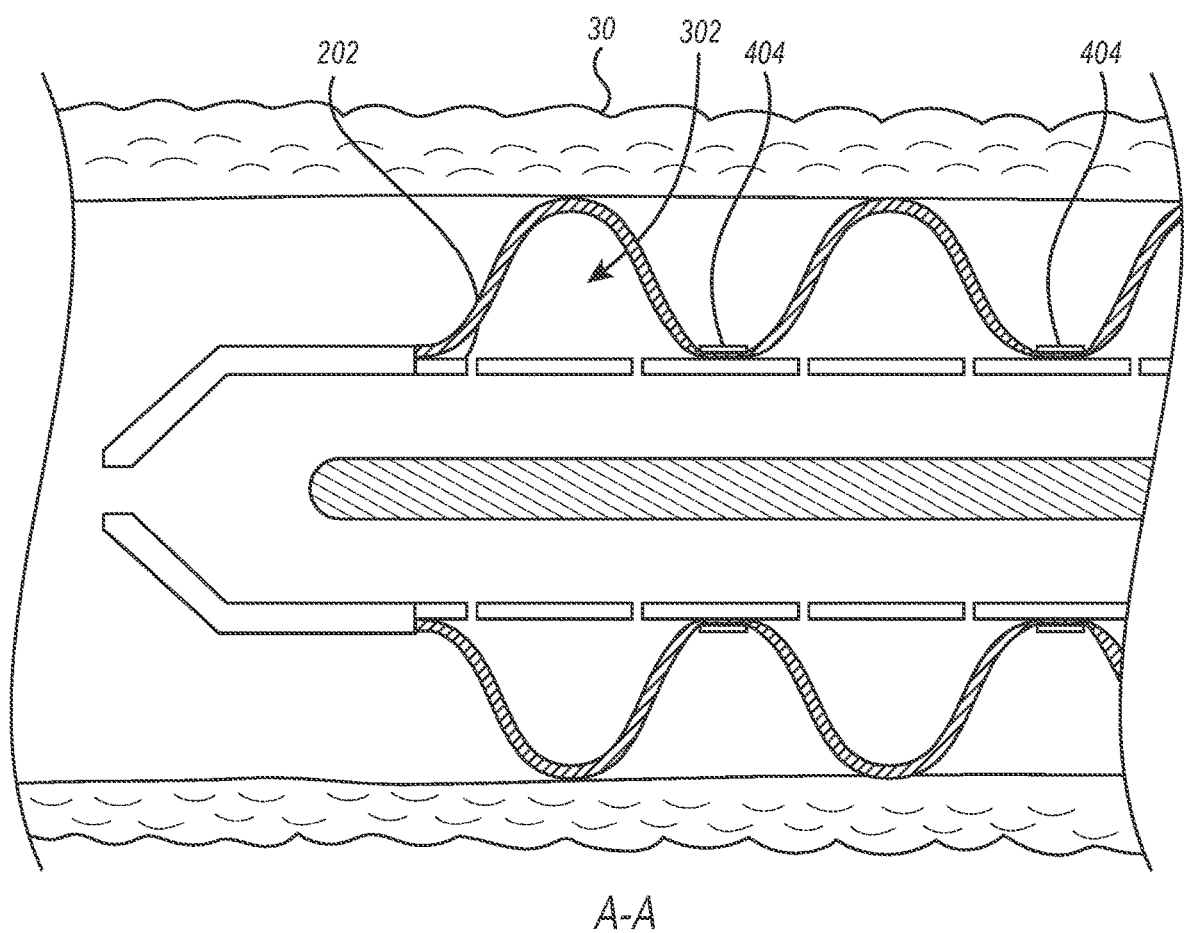
FIG. 7B illustrates a transverse cross-sectional view thereof.

FIG. 7B illustrates another cross-sectional view of the sheath 700 disposed within a vascular conduit 10. The elongate members 402 have been extended radially outwardly from the body 102 to push against the vascular wall 300 and create space 302 between the sheath 700 and vascular wall 30. As discussed above, the support regions 404 restrain portions of the elongate member 402 from extending radially from the body 102.

Figure 8:
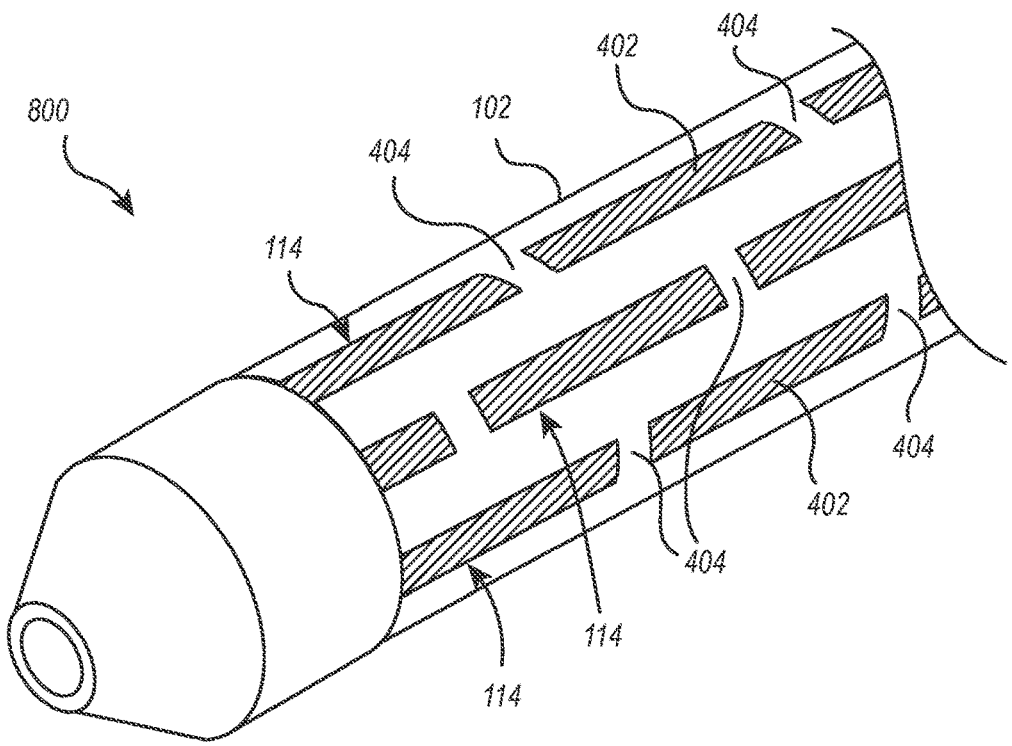
FIG. 8 illustrates a perspective view of the distal end of a procedural sheath according an embodiment of the present disclosure.

One will appreciate that a number of channel 114 configurations and patterns may be implemented, which achieve the same function as the channels 114 already herein described. For example, FIG. 8 illustrates a number of elongate members 402 received into channels 114 disposed along the working length of an embodiment of a sheath 800. In this embodiment, portions of the elongate members 402 disposed between support regions 404 are staggered relative to parallel elongate member 402 portions. This is due to the staggered pattern of support regions 404 around the circumference and along the working length of the body 102.

Figure 9:
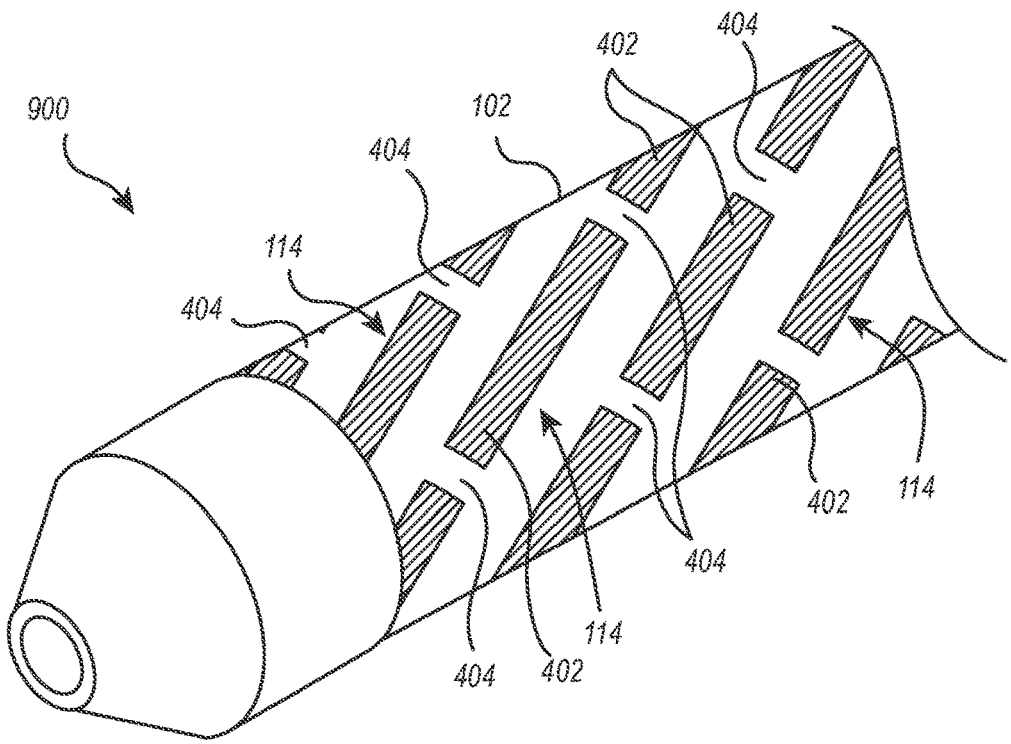
FIG. 9 illustrates a perspective view of the distal end of a procedural sheath according an embodiment of the present disclosure.

Alternatively, FIG. 9 illustrates a helical pattern of channels 114, elongate members 402, and support regions 404, disposed around the circumference and along the working length of the body 102 of a sheath 900. In the illustrated embodiment, the channels 114 and elongate members 402 wrap around the body 102 at an angle, forming a helical pattern. Additionally, or alternatively, the support regions 404 may be staggered so that they do not align with support regions 404 that span parallel channels 114.

Figure 10:
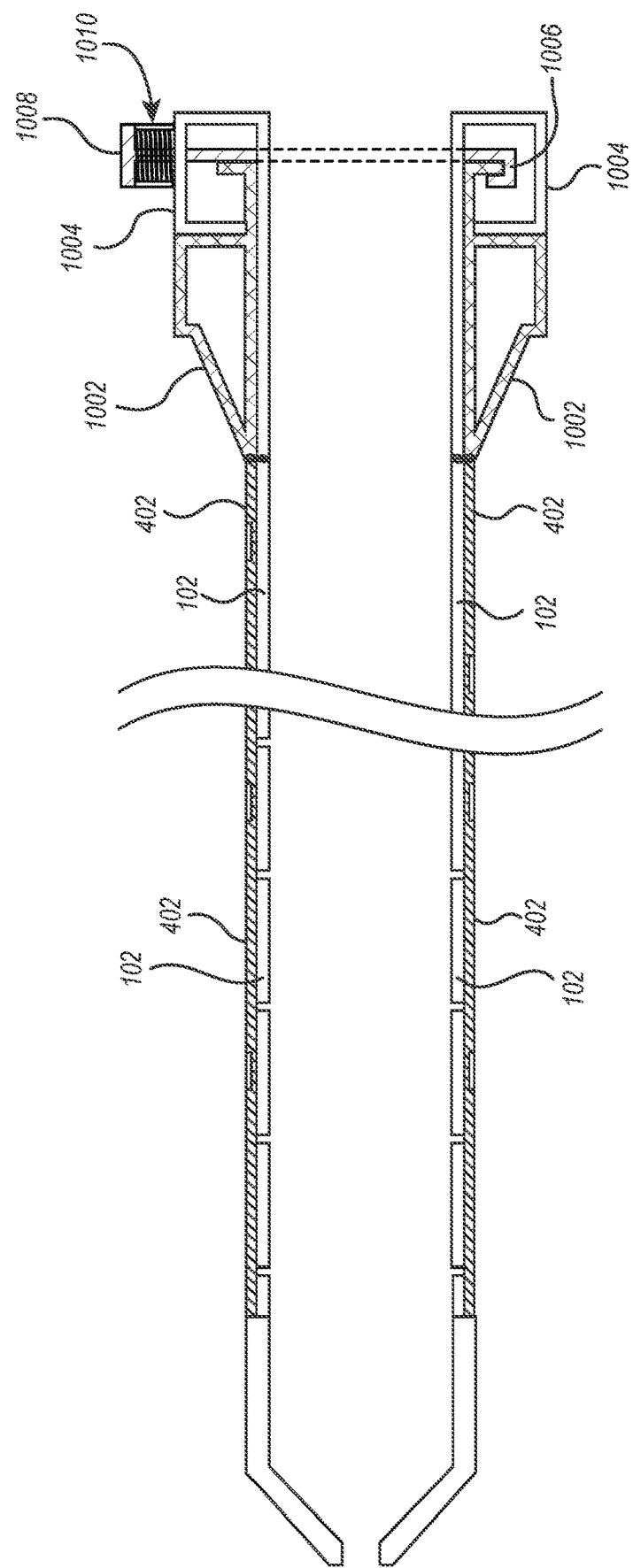
FIG. 10 illustrates a longitudinal cross-sectional view of a procedural sheath according to an embodiment of the present disclosure.
Figure 11:
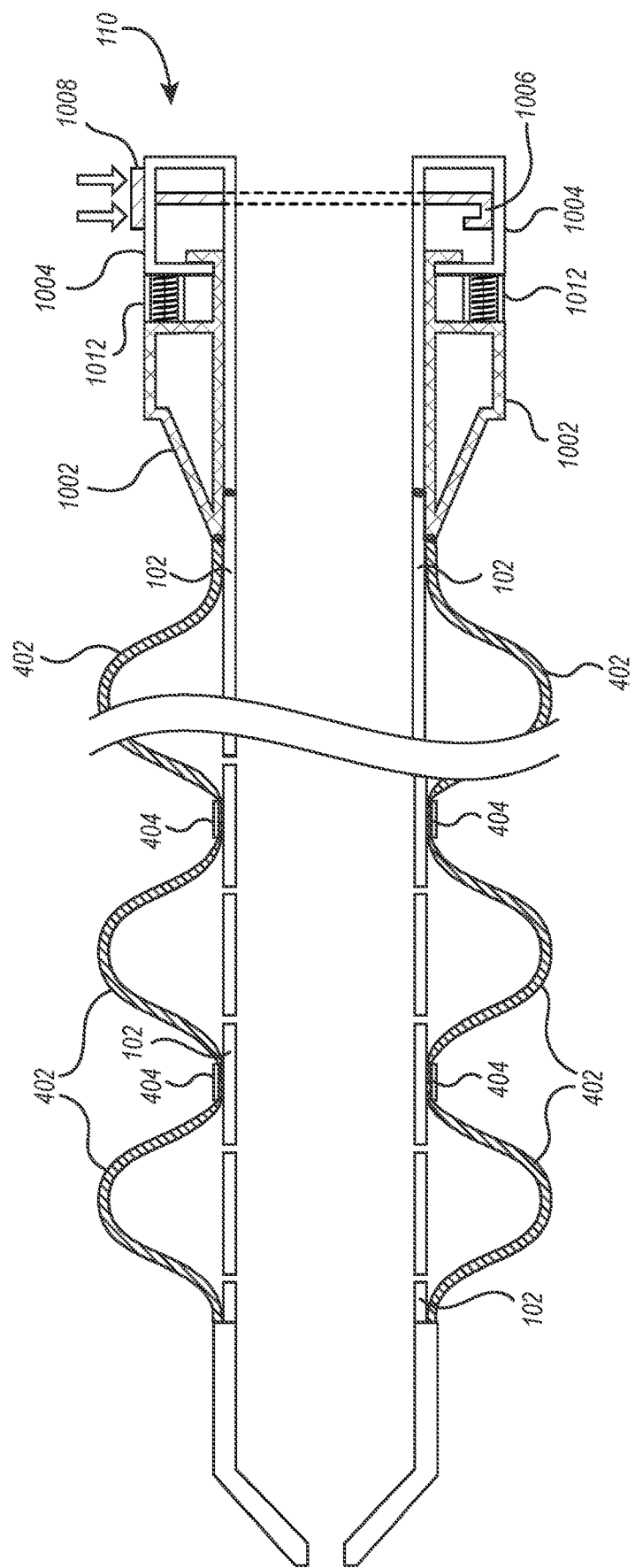
FIG. 11 illustrates a longitudinal cross-section view of a procedural sheath according to an embodiment of the present disclosure.

FIGS. 10 and 11 illustrate how the elongate members 402 may be selectively moved to extend radially outwardly from the body 102 of a sheath. As discussed above with reference to FIG. 1, a hub 110 may be disposed at the proximal end 104 of the sheath 100. A cross-sectional view of an embodiment of a hub 110 is illustrated in FIGS. 10 and 11 is similar to the hub 110 of FIG. 1. In the illustrated embodiment, the hub 110 may include a first portion 1002 and a second portion 1004. The first portion 1002 may be rigidly attached to the elongate members 402 and the second portion 1004 may be rigidly attached to the body 102. In FIG. 10, the hub 110 is configured so that the elongate members 402 do not extend radially outwardly from the body 102.

In one embodiment, the first portion 1002 and the second portion 1004 of the hub 110 may be biased away from one another but held together, as shown in FIG. 10, via a clip 1006 that prevents the first portion 1002 from moving distally away from the second portion 1004. The clip 1006 may be manipulated by a push tab 1008 that retains the clip 1006 around the first portion 1002 and locks the first portion 1002 to the second portion 1004 of the hub. The push tab 1008 may be biased to rest in the position illustrated in FIG. 10 by a biasing member 1010 that maintains the locked configuration shown.

FIG. 11 illustrates how a manipulation of the hub 110 may selectively move the elongate members radially outwardly from the body 102. For example, in the illustrated embodiment, the push tab 1008 may be pressed downward, as indicated by the arrows above the push tab 1008. The clip 1006 is subsequently pushed down to release the clip from the first portion 1002. As discussed above, the first portion 1002 may be biased away from the second portion 1004 by one or more biasing members 1012. Thus, in the illustrated embodiment, when the push tab 1008 is moved down, the clip 1006 releases the first portion 1002 and the one or more biasing members 1012 move the first portion 1002 distally from the second portion 1004.

As noted above, the first portion 1002 may be secured to the elongate members 402 and the second portion may be secured to the second portion 1004. Thus, when the first portion 1002 of the hub 110 moves distally from the second portion 1004 of the hub 110, the total longitudinal distance between the tip 116 of the sheath 100, where the elongate members 402 may terminate distally, and the first portion 1002 is reduced relative to the distance between the tip 116 and the second portion 1004. In this configuration, the elongate members 402 may tend to bend or extend radially outwardly from the body 102. Specifically, the elongate members 402 may extend radially outwardly from the body between the support regions 404 as illustrated in FIG. 11. In this way, the elongate members 114 may operatively cooperate with the channels 114 to fluidly control fluid access into the device receiving lumen 208 of the body 102 through the plurality of fluid paths 202 by selectively closing the inlets 204.

In one embodiment of the present invention, the elongate members 402 may be heat set expanded at portions along the length of the elongate members 402 that lie between adjacent support regions 404. The heat set expansion may be done while the first and second portions 1002, 1004 of the hub 110 are separated, so as to allow the elongate members 402 to expand outwardly, as described above. In this embodiment, the elongate members 402 would be expanded outwardly in an initial state. In preparation for insertion of the sheath into the vasculature of a patient, the elongate members 402 may be pulled inwardly towards the body 102 of the sheath 100. Pulling the elongate members 402 inwardly toward the body 102 may be done, for example, by manipulating the hub 110 so that the first portion 1002 is connected to the second portion 1004, as described above.

Along these lines, once the sheath 100 has been inserted into the vasculature of a patient, the first portion 1002 of the hub 110 can be gradually released to move distally from the second portion 1004 of the hub 110, resulting in the elongate members 402 returning to the initial expanded state as shown in FIG. 11. Such an embodiment, including the heat set elongate members 402 described above, may ensure that each elongate member 402 expands consistently from one portion between adjacent support regions 404 to another. That is, each portion of elongate member 402, which are disposed between two adjacent support regions 404, may expand the substantially same distance away from the body 102 between each support region 202.

Figure 12:
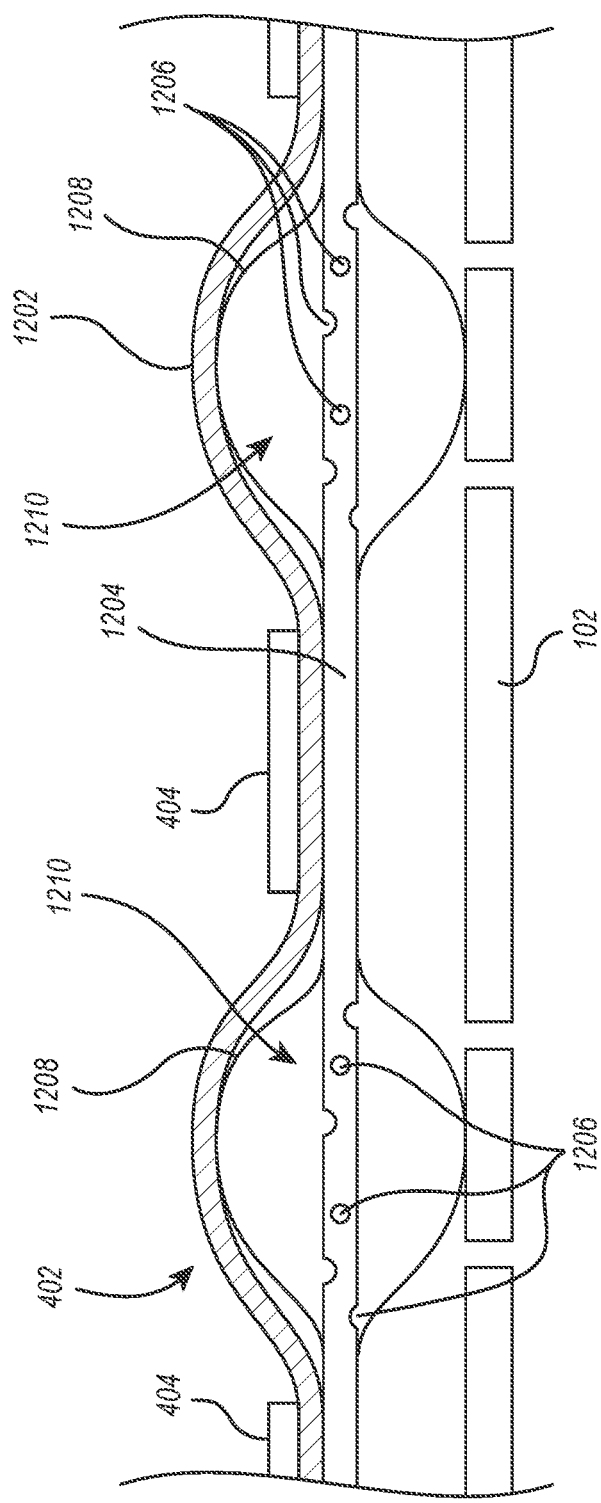
FIG. 12 illustrates a longitudinal cross-section view of an elongate member according to an embodiment of the present disclosure.

FIG. 12 illustrates a longitudinal cross-section view of yet another embodiment of an elongate member 402 that may also ensure equal expansion of the elongate members 402 between support regions 404 along the length of the body 102. In the illustrated embodiment, each elongate member 402 comprises a thin ribbon 1202 and an inflation tube 1204 disposed between the ribbon 1202 and the body 102.

In the illustrated embodiment, the inflation tube 1204 may include one or more holes 1206 and a ballooning membrane 1208 disposed over the holes 1206. The holes 1206 and ballooning membrane 1208 of the inflation tube 1204 may be positioned between adjacent support regions 404 along the length of the body 102. In this embodiment, a fluid or gas may pass through the inflation tube 1204 and exit the holes 1206 to inflate the ballooning membrane 1208, creating a balloon 1210 between the ribbon 1202 and body 102. The balloons 1210 may inflate between adjacent support regions 404, thus pushing portions of the ribbon 1202 outwardly from the body 102 between the support regions 1202.

In such an embodiment, the first portion 1002 of the hub 110 may first be moved distally from the second portion 1004 of the hub 110 before expansion of the balloons 12010. This would allow the ribbon 1202 of the elongate member 402 to freely move relative to the body 102. As such, the balloons 1210 may push portions of the ribbon 1202 outwardly from the body 102 between support regions 404, as described above and shown in FIG. 12.

Figure 13:
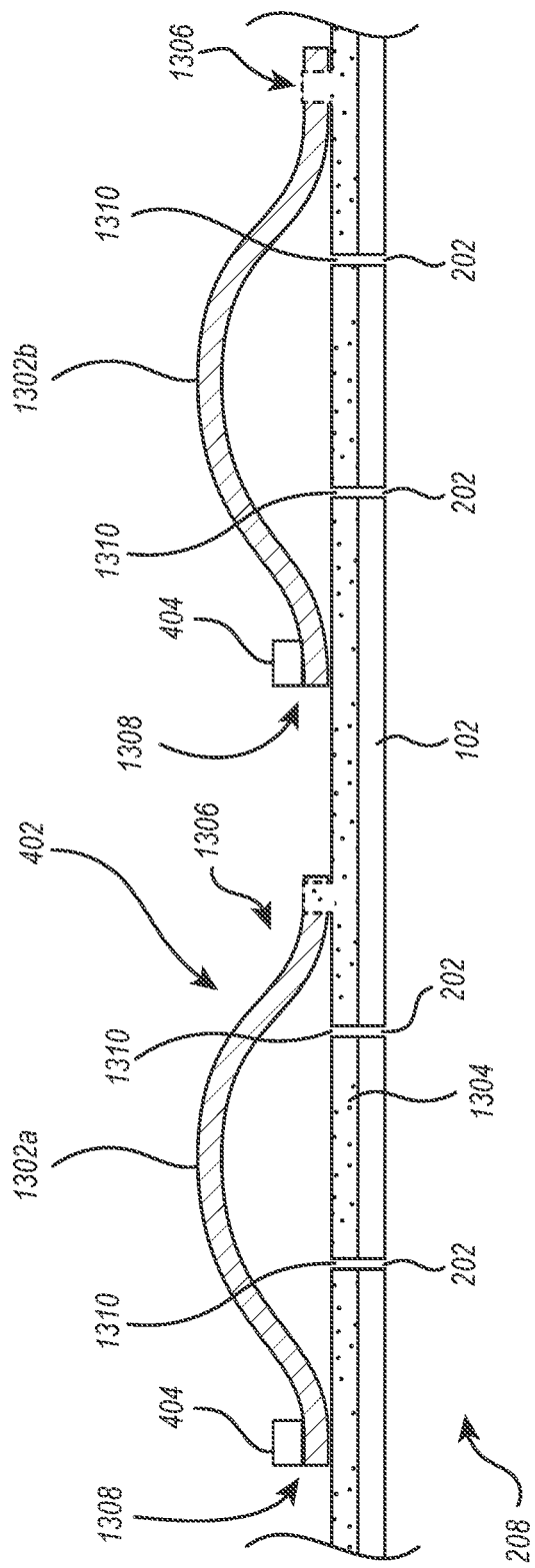
FIG. 13 illustrates a longitudinal cross-section view of an elongate member expanded outwardly from the body of a sheath according to an embodiment of the present disclosure.
Figure 14:
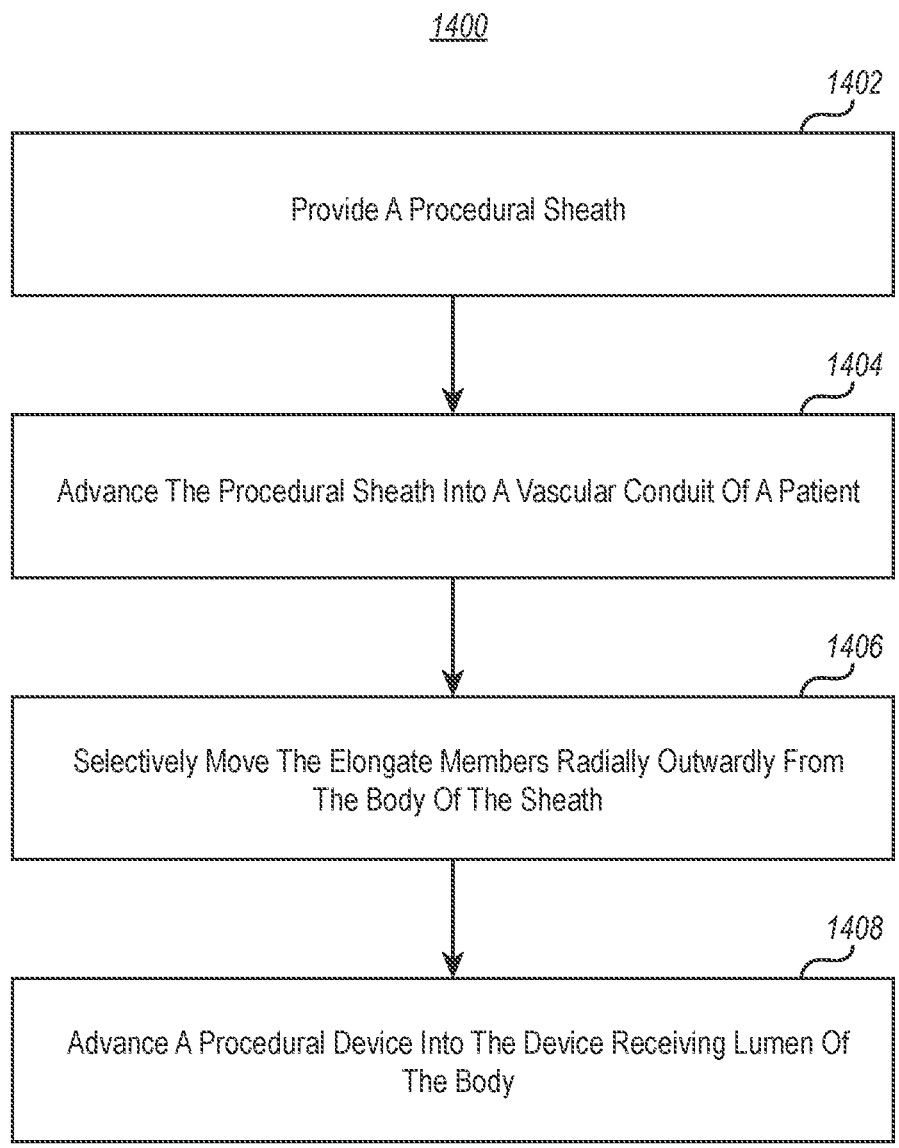
FIG. 14 illustrates a schematic representation of a method for performing a procedure using a procedural device according to the present disclosure.

FIG. 13 also shows an embodiment of an elongate member 402 that may ensure equal expansion between support regions 404 along the length of the body 102. For example, FIG. 13 illustrates an elongate member 402 that comprises a plurality of thin ribbon sections 1302a, 1302b and an elongate active member 1304. In one embodiment, the active member 1304 may be secured to the first portion 1002 of the hub 110 and be moveable relative to the body 102. Also, the active member 1304 may be rigidly secured to a proximal end 1306 of each of the ribbon sections 1302a, 1302b. In the illustrated embodiment of FIG. 13, the active member 1304 is rigidly attached to the ribbon sections 1302a, 1302b by extending up through the ribbon sections 1302a, 1302b. In one or more other embodiments, the active member 1304 may be rigidly secured to each ribbon section 1302a, 1302b in various other ways. For example, in one embodiment, the active member 1304 may be adhered using an adhesive or welded to the proximal end 1306 of each ribbon section 1302a, 1302b.

Furthermore, in one embodiment, the distal end 1308 of each ribbon section 1302a, 1302b may be rigidly secured to a support region 404. In this way, as shown in the expanded configuration illustrated in FIG. 13, a distal movement of the active member 1304 relative to the body 102 and support regions 404 may cause each ribbon section 1302a, 1302b of the elongate member to expand outwardly from the body 102 when the first portion 1002 of the hub 110 is moved distally from the second portion 1004 of the hub 110.

FIG. 13 also shows an embodiment of an active member 1304 that includes one or more fluid paths 1310 that correspond in position to the fluid paths 202 of the body 102 when the ribbon sections 1302a, 1302b have been extended outwardly from the body 102. In such an embodiment, fluid, such blood flowing through the vasculature of a patient, may pass through fluid paths 1310 and 202 from outside the body 102 of the sheath into the device receiving lumen 208, as described with reference to other embodiments described above.

Accordingly, when the first portion 1002 of the hub 110 is not moved distally from the second portion 1004 of the hub 100, the fluid paths 1310 of the active member 1304 may not align with the fluid paths 202 of the body 202. Thus, if the first portion 1002 of the hub 110 is still connected to, or has been returned to, the second portion 1004 of the hub 110, the ribbon sections 1302a, 1302b will cover the fluid paths 1310 and the fluid paths 1310 of the active member 1304 will not align with the fluid paths 202 of the body 102, thus blocking fluid flow into the device receiving lumen 208.

In any of the embodiments described above, the elongate members 402 may be selectively returned to the body 102 after being extended outwardly by locking the first and second portions 1002, 1004 of the hub 110 back together. This may be accomplished by pressing the two portions 1002, 1004 together while simultaneously pressing the push tab 1008 down. The push tab 1008 may then be released so that the clip 1006 prevents the first portion 1002 from moving distally away from the second portion 1004, as illustrated in FIG. 10. It will be appreciated that the push tab 1008 may be manipulated in a variety of other way, such as, for example, pneumatically, hydraulically, magnetically, or the like. Also, the clip 1006 and first and second portions 1002, 1004 may take various other forms and configurations in other embodiments while still performing the same functions as described herein.

In light of the foregoing description, a method 1400 of performing an intravascular procedure, while maintaining a fluid path through a vascular conduit of a patient may include a first step 1402 of providing a procedural sheath as described herein. Next, the method 1400 may include the step 1404 of advancing the procedural sheath into a vascular conduit of a patient. The method 1400 may also include the step 1406 of selectively moving the elongate members of the procedural sheath radially outwardly from the body of the sheath. Furthermore, the method 1400 may include a step 1408 comprising advancing a procedural device into the device receiving lumen of the body.

Additionally, the method may include further steps of withdrawing the procedural device from the device receiving lumen and moving the elongate member radially inwardly toward the body of the sheath. The procedural sheath may then be withdrawn from the vascular conduit of the patient.

In order to advance the procedural sheath into a vascular conduit of a patient, a medical professional may first create an insertion site for access into the vasculature of a patient as required by a wide range of procedures. As discussed above, such procedures may range from those that require extended periods time inside the vasculature of a patient as well as insertion into small diameter vasculature in the patient's extremities. For example, the procedural sheath of the present disclosure may be inserted into the femoral artery of a patient and advanced through the conduit of the femoral artery to the heart. Also, for example, the procedural sheath of the present disclosure may be inserted into the vasculature anterior to the knee of a patient and advanced distally through the vasculature towards the patient's ankle or foot.

In one implementation of the method described herein, the procedural device may include a guidewire. In one embodiment, the procedural device may include an embolic catheter used for the delivery of embolic coils to occlude embolisms. In yet another embodiment, the procedural device may include a balloon catheter configured to deliver a stent or valve into the vasculature surrounding the heart. One will appreciate that numerous procedural devices may be advance through the procedural sheath of the present disclosure according to various embodiments of the method described herein.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A procedural sheath comprising:
   an elongate body having a proximal end, a distal end, a device receiving lumen extending from the proximal end to the distal end, and a channel extending along a working length of the body, the channel comprising a first end region and a second end region, the device receiving lumen being generally uniform in diameter along the working length of the body;
   an elongate member selectively disposed within the channel of the body; and
   a plurality of fluid paths formed in a base of the channel, each of the plurality of fluid paths includes an inlet in the base of the channel and an outlet at the device receiving lumen,
   wherein the elongate member operatively cooperates with the channel and fluidly controls fluid access into the device receiving lumen of the body through the plurality of fluid paths by selectively opening and closing the inlets, wherein an intermediate portion of the elongate member, between the first end region and the second end region, is configured to protrude outwardly from within the channel during selective opening and closing of the inlets, and wherein a first portion of the elongate member extended towards the first end region and a second portion of the elongate member extended towards the second end region remains within the channel.

2. The procedural sheath of claim 1, wherein the channel extends longitudinally along at least about 70% of the working length of the body.

3. The procedural sheath of claim 1, wherein the device receiving lumen has a diameter of at least about 0.31 inches.

4. The procedural sheath of claim 1, wherein an outer diameter of the body is between about 0.36 inches and 0.47 inches.

5. The procedural sheath of claim 1, wherein the elongate member selectively moves between about 0.5 mm and 1.5 mm radially outwardly from the body.

6. The procedural sheath of claim 5, further comprising a hub operatively coupled to the proximal end of the body, wherein a manipulation of the hub selectively moves the elongate member radially outwardly from the body.

7. The procedural sheath of claim 1, further comprising a plurality of supporting regions arranged along the channel region.

8. The procedural sheath of claim 7, wherein each supporting region overlaps at least a portion of the elongate member and limits radial movement of the elongate member.

9. The procedural sheath of claim 8, wherein a portion of the elongate member between two adjacent supporting regions selectively moves between about 0.5 mm and 1.5 mm radially outwardly from the body.

10. The procedural sheath of claim 1, wherein the body comprises a plurality of channel regions and a plurality of elongate members, the plurality of channel regions extending along a working length of the body.

11. A large-bore procedural sheath comprising:
a body comprising a proximal end, a distal end, and a length extending therebetween;
a plurality of channels on an exterior surface of the body extending longitudinally along at least about 70% of the length of the body, each of the plurality of channels comprising a first end region and a second end region;
a device receiving lumen having a substantially uniform diameter along a length of the device receiving lumen from the proximal end to the distal end of the body, the lumen configured to receive a procedural device therein;
a plurality of fluid paths formed in each channel of the plurality of channels, each of the plurality of fluid paths comprising an inlet formed at one of the plurality of channels and an outlet formed at the device receiving lumen, wherein the device receiving lumen fluidly communicates with the plurality of channels through the plurality of fluid paths; and
a plurality of elongate members that are selectively disposed within the plurality of channels, each elongate member operatively cooperating with a channel of the plurality of channels to fluidly control fluid access into the device receiving lumen of the body through the plurality of fluid paths by selectively opening and closing the inlets, wherein an intermediate portion of the elongate member, between the first end region and the second end region, is configured to protrude outwardly from within the channel during selective opening and closing of the inlets, and wherein a first portion of the elongate member extended towards the first end region and a second portion of the elongate member extended towards the second end region remains within the channel.

12. The large-bore procedural sheath of claim 11, the body further comprising a wall having a thickness between about 0.05 inches and 0.1 inches extending from the exterior surface of the body to the device receiving lumen.

13. The large-bore procedural sheath of claim 12, wherein each of the plurality of channel regions comprises a recessed portion extending into the wall from the exterior surface of the body, a depth of the recessed portion being between about 0.04 inches and 0.9 inches.

14. The large-bore procedural sheath of claim 13, wherein the wall maintains a radial force transferred to the body of between 1 Newton and 7 Newtons.

15. The large-bore procedural sheath of claim 11, wherein an outer diameter of the body is between about 0.36 inches and 0.47 inches.

16. The large-bore procedural sheath of claim 11, wherein the device receiving lumen has a diameter of between about 0.31 inches and 0.37 inches.

17. The large-bore procedural sheath of claim 11, wherein each fluid path comprises a perforation.

18. A procedural sheath comprising:
a body having a length extending between a proximal end and a distal end thereof;
a device receiving lumen extending longitudinally inside the body, the device receiving lumen having a substantially uniform diameter along a length of the lumen from the proximal end to the distal end of the body;
a channel extending on the surface of the body longitudinally along at least about 70% of the length of the body;
a plurality of support regions disposed along a length of the channel;
a plurality of fluid paths formed between the channel and the device receiving lumen;
an elongate member; and
a hub coupled to the proximal end of the body, the hub being configured to selectively move the elongate member between a first configuration and a second configuration,
wherein, in the first configuration, the elongate member is received within the channel and the elongate member covers the plurality of fluid paths in the channel so that the device receiving lumen does not fluidly communicate with the channel through the plurality of fluid paths, and
wherein, in the second configuration, portions of the elongate member that are disposed between support regions along the length of the channel extend radially outward from the channel, the elongate member being in the second configuration and uncovering the plurality of fluid paths in the channel so that the device receiving lumen fluidly communicates with the channel through the plurality of fluid paths and the elongate member exerts a force against an interior surface of a vascular wall.

19. The procedural sheath of claim 18, wherein each of the plurality of fluid paths includes an inlet at the channel and an outlet at the device receiving lumen.

20. The procedural sheath of claim 18, wherein each elongate member comprises a shape memory material.

21. The procedural sheath of claim 18, wherein each support region overlaps at least a portion of the elongate member and limits radial movement of the elongate member.

22. The procedural sheath of claim 18, wherein the channel extends helically around the body.

23. A method for performing an intravascular procedure while maintaining a fluid path through a vascular conduit, comprising:
 providing a procedural sheath, the procedural sheath comprising:
  a body comprising a channel with a plurality of fluid paths formed in a base of the channel, each of the plurality of fluid paths including an inlet in the base of the channel and an outlet at a device receiving lumen of the body, the device receiving lumen being generally uniform in diameter along the length of the body;
  an elongate member selectively coupled to the body, the elongate member operatively cooperating with the channel and fluidly controlling fluid access into the device receiving lumen of the body through the plurality of fluid paths by selectively closing the inlets;
 advancing the procedural sheath into the vascular conduit;
 moving the elongate member radially outwardly from the body to push radially outwardly on an inside surface of the conduit and allow fluid access into the device receiving lumen of the body; and
 advancing a procedural device into the device receiving lumen of the body.

24. The method of claim 23, further comprising:
 withdrawing the procedural device;
 moving the elongate member radially inwardly toward the body; and
 withdrawing the procedural sheath from the vascular conduit of the patient.

25. The method of claim 23, further comprising:
 before advancing the procedural sheath into the vascular conduit, creating an insertion site for access to a femoral artery;
 wherein advancing the procedural sheath into the vascular conduit comprises advancing the procedural sheath toward a heart.

26. The method of claim 23, further comprising:
 before advancing the procedural sheath into the vascular conduit, creating an insertion site for access to vasculature that is anterior to a knee;
 wherein advancing the procedural sheath into the vascular conduit comprises advancing the procedural sheath toward an ankle or foot.

27. The method of claim 23, wherein the procedural device comprises a guidewire.

28. The method of claim 23, wherein the procedural device comprises a catheter configured to perform an embolism occlusion procedure.

29. The method of claim 23, wherein the procedural device comprises a balloon catheter.

30. The method of claim 23, wherein moving the elongate member radially outwardly from the body comprises manipulating a hub disposed at a proximal end of the body.

* * * * *